US012606823B2

(12) United States Patent
Lee

(10) Patent No.: US 12,606,823 B2
(45) Date of Patent: Apr. 21, 2026

(54) MODIFIED CPF1 GUIDE RNA

(71) Applicant: Breeze Bio, Inc., South San Francisco, CA (US)

(72) Inventor: Kunwoo Lee, South San Francisco, CA (US)

(73) Assignee: Breeze Bio, Inc.

( * ) Notice: Subject to any disclaimer, the term of this patent is extended or adjusted under 35 U.S.C. 154(b) by 1050 days.

(21) Appl. No.: 16/753,293

(22) PCT Filed: Oct. 2, 2018

(86) PCT No.: PCT/US2018/054027

§ 371 (c)(1),
(2) Date: Apr. 2, 2020

(87) PCT Pub. No.: WO2019/070762

PCT Pub. Date: Apr. 11, 2019

(65) Prior Publication Data

US 2020/0299689 A1 Sep. 24, 2020

Related U.S. Application Data

(60) Provisional application No. 62/697,327, filed on Jul. 12, 2018, provisional application No. 62/617,138, filed on Jan. 12, 2018, provisional application No. 62/567,123, filed on Oct. 2, 2017.

(51) Int. Cl.
*C12N 15/113* (2010.01)
*C12N 15/88* (2006.01)

(52) U.S. Cl.
CPC ............ *C12N 15/113* (2013.01); *C12N 15/88* (2013.01); *C12N 2310/20* (2017.05); *C12N 2310/315* (2013.01); *C12N 2310/321* (2013.01); *C12N 2310/531* (2013.01)

(58) Field of Classification Search
CPC .. C12N 15/113; C12N 15/88; C12N 2310/20; C12N 2310/315; C12N 2310/321; C12N 2310/531
See application file for complete search history.

(56) References Cited

U.S. PATENT DOCUMENTS

| | | | |
|---|---|---|---|
| 2014/0349400 | A1 | 11/2014 | Jakimo et al. |
| 2016/0289675 | A1 | 10/2016 | Ryan et al. |

FOREIGN PATENT DOCUMENTS

| | | | |
|---|---|---|---|
| CN | 106 244 591 | A | 12/2016 |
| WO | WO 2013/176772 | A1 | 11/2013 |
| WO | WO 2015/013583 | A2 | 1/2015 |
| WO | WO 2015/035139 | A2 | 3/2015 |
| WO | WO 2016/022866 | A1 | 2/2016 |
| WO | WO 2016/028843 | A2 | 2/2016 |
| WO | WO 2016/065364 | A1 | 4/2016 |
| WO | WO 2016/094867 | A1 | 6/2016 |
| WO | WO 2016/182959 | A1 | 11/2016 |
| WO | WO 2016/183402 | A2 | 11/2016 |
| WO | WO 2017/040511 | A1 | 3/2017 |
| WO | WO 2017/053312 | A1 | 3/2017 |
| WO | WO 2017/064546 | A1 | 4/2017 |
| WO | WO 2017/070598 | A1 | 4/2017 |
| WO | WO 2017/180711 | A1 | 10/2017 |
| WO | WO 2017/186550 | A1 | 11/2017 |
| WO | WO 2017/207589 | A1 | 12/2017 |
| WO | WO 2018/094356 | A2 | 5/2018 |
| WO | WO 2018/204493 | | 8/2018 |
| WO | WO 2019/070762 | A1 | 4/2019 |

OTHER PUBLICATIONS

Dehua et al. CN 106244591 (2016), pp. 1-14, WIPO machine translation retrieved Jun. 2023 (Year: 2016).*

Olejnik et al. (Nucleic Acids Research (1996) vol. 24, No. 2, pp. 361-366). (Year: 1996).*

Jiang, Yu et al., "CRISPR-Cpf1 assisted genome editing of *Corynebacterium glutamicum*," Nature Communications, vol. 8, pp. 15179:1-11, p. 4; Fig. 1b (2017).

Park, Hyo Min et al., "Extension of the crRNA enhances Cpf1 gene editing in vitro and in vivo," *Nature Communications*, vol. 9, No. 1, pp. 3313: 1-12 (2018).

First Written Opinion and Search Report issued in Application No. 11202003083P by the Intellectual Property Office of Singapore on Sep. 27, 2021.

Fontara, Ines et al., "The CRISPR-associated DNA-cleaving enzyme Cpf1 also processes precursor CRISPR RNA", *Nature*, vol. 532, pp. 517-521 (2016).

Zuris JA, et al., "Cationic lipid-mediated delivery of proteins enables efficient protein-based genome editing in vitro and in vivo," *Nat. Biotech*, 33(1): pp. 73-80 (2015).

Schaffer DV et al., "Vector unpacking as a potential barrier for receptor-mediated polyplex gene delivery," *Biotechnol Bioeng*, 67(5): pp. 598-606 (2000).

Ousterout DG, et al., "Multiplex CRISPR/Cas9-based genome editing for correction of dystrophin mutations that cause Duchenne Muscular Dystrophy," *Nat. Commun*, 6:6244 (2015).

Durand G., et al., "A combinatorial approach to the repertoire of RNA kissing motifs; towards multiplex detection by switching hairpin aptamers," *Nucleic Acids Res.*, vol. 44(9): pp. 4450-4459 (2016).

(Continued)

*Primary Examiner* — J. E. Angell

(74) *Attorney, Agent, or Firm* — Leydig, Voit & Mayer, Ltd.

(57) ABSTRACT

The invention provides a nucleic acid comprising a Cpf1 crRNA, a processing sequence 5' of the Cpf1 crRNA, and an extension sequence 5' of the processing sequence. The invention also provides a composition comprising the nucleic acid, a carrier, and optionally Cpf1. Additionally, the invention provides method of genetically modifying a eukaryotic target cell, comprising contacting the eukaryotic target cell with the nucleic acid or the composition to genetically modify a target nucleic acid in the cell.

29 Claims, 31 Drawing Sheets

Specification includes a Sequence Listing.

(56) References Cited

OTHER PUBLICATIONS

Shu D., et al., "Thermodynamically stable RNA three-way junctions as platform for constructing multi-functional nanoparticles for delivery of therapeutics," *Nat. Nanotechnol.*, vol. 6(10): pp. 658-667 (2011).
Yu J., et al., "De novo design of an RNA tile that self-assembles into a homo-octameric nanoprism," *Nat. Commun.* vol. 6:5724 (2014).
Sobczak, et al., "Structural Diversity of Triplet Repeat RNAs," *J. Biol. Chem.*, vol. 285(17): pp. 12755-12764 (2010).
Nowak, C. M. et al., "Guide RNA engineering for versatile Cas9 functionality," *Nucleic Acids Research*, vol. 44, No. 20, pp. 9555-9564 (2016).
Kelley, M. L. et al., "Versatility of chemically synthesized guide RNAs for CRISPR-Cas9 genome editing," *Journal of Biotechnology*, vol. 233, pp. 74-83 (2016).
Lee, K. et al., "Synthetically modified guide RNA and donor DNA are a versa title platform for CRISPR-Cas9 engineering," *eLife*, vol. 6 Article No. e25312, pp. 1-17 (2017).
Jinek et al., "RNA-programmed genome editing in human cells", *eLIFE, eLIFE Sciences Publications Ltd.*, vol. 2 (2013).
Yu et al., "Small Molecules Enhance CRISPR Genome Editing in Pluripotent Stem Cells", *Cell Stem Cell*, vol. 16, No. 2, pp. 142-147 (2015).
Pinder et al., "Nuclear domain 'knock-in' screen for the evaluation and identification of small molecule enhancers of CRISPR-based genome editing", Nucleic Acids Research, vol. 43, No. 19, pp. 9379-9392 (2015).
European Search Report in Application No. 17870720.4 mailed Jun. 30, 2020.
International Search Report and Written Opinion issued in PCT/US2018/054027 mailed Dec. 17, 2018.
Xu et al., "Generation of targeted mutant rice using a CRISPR-Cpf1 system", *Plant Biotechnology Journal*, vol. 15, No. 6, pp. 713-717 (Jun. 1, 2017).
Li, et al., "Engineering CRISPR-Cpf1 crRNAs and mRNAs to maximize genome editing efficiency", *Nature biomedical engineering*, vol. 1, No. 5, pp. 1-21 (May 10, 2017).
Dang et al., "Optimizing sgRNA structure to improve CRISPER-Cas9 knockout efficiency", *Genome Biology*, vol. 16, No. 280, pp. 1-10 (Jan. 1, 2015).
Zetsche et al., "Cpf1 Is a Single RNA-Guided Endonuclease of a Class 2 CRISPR-Cas System", *Cell*, vol. 163, No. 3, pp. 759-771 (Oct. 1, 2015).
Sternberg et al., "Mechanism of substrate selection by a highly specific CRISPR endoribonuclease," RNA, 18: 661-672 (2012).
Nishimasu et al., "Crystal Structure of Cas9 in Complex with Guide RNA and Target DNA," *Cell*, 156: 935-949 (Feb. 2014).

* cited by examiner

FIG. 5A
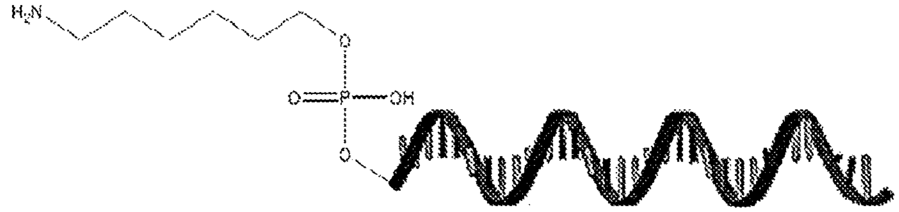
5′ Amine crRNA
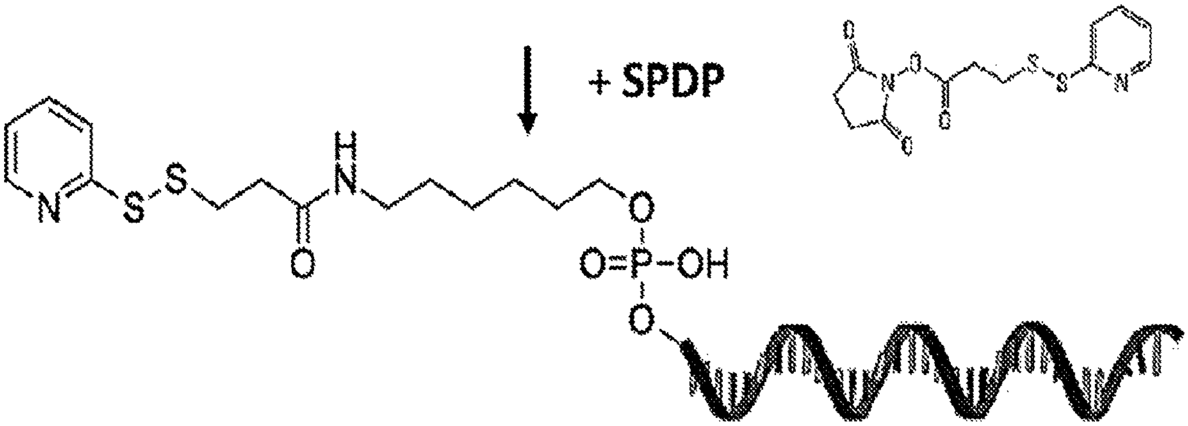
5′ Thiopyridyl crRNA
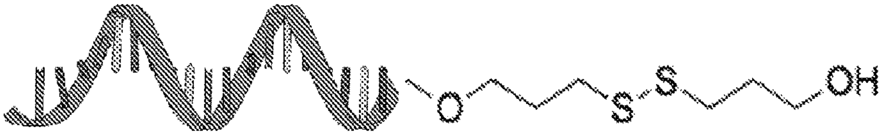
3′ Disulfide Donor DNA
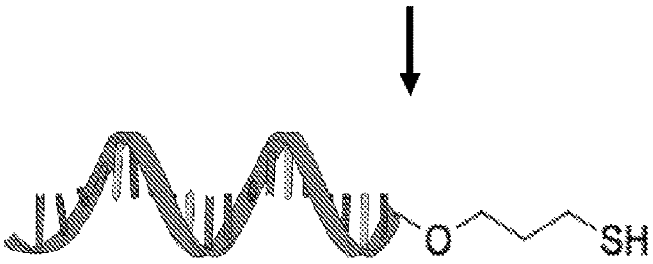
3′ Thiol Donor DNA

Figure 8

Francisella tularensis subsp. novicida U112 Cpf1

```
   1 msiyqefvnk yslsktlrfe lipqgktlen ikarglildd ekrakdykka kqiidkyhqf
  61 fieeilssvc isedllqnys dvyfklkksd ddnlqkdfks akdtikkqis eyikdsekfk
 121 nlfnqnlida kkgqesdlil wlkqskdngi elfkansdit didealeiik sfkgwttyfk
 181 gfhenrknvy ssndiptsii yrivddnlpk flenkakyes lkdkapeain yeqikkdlae
 241 eltfdidykt sevnqrvfsl devfeianfn nylnqsgitk fntiiggkfv ngentkrkgi
 301 neyinlysqq indktlkkyk msvlfkqils dtesksfvid kleddsdvvt tmqsfyeqia
 361 afktveeksi ketlsllfdd lkaqkldlsk iyfkndkslt dlsqqvfddy svigtavley
 421 itqqiapknl dnpskkeqel iakktekaky lsletiklal eefnkhrdid kqcrfeeila
 481 nfaaipmifd eiaqnkdnla qisikyqnqg kkdllqasae ddvkaikdll dqtnnllhkl
 541 kifhisqsed kanildkdeh fylvfeecyf elanivplyn kirnyitqkp ysdekfklnf
 601 enstlangwd knkepdntai lfikddkyyl gvmnkknnki fddkaikenk gegykkivyk
 661 llpgankmlp kvffsaksik fynpsedilr irnhsthtkn gspqkgyekf efniedcrkf
 721 idfykqsisk hpewkdfgfr fsdtqrynsi defyrevenq gykltfenis esyidsvvnq
 781 gklylfqiyn kdfsayskgr pnlhtlywka lfdernlqdv vyklngeael fyrkqsipkk
 841 ithpakeaia nknkdnpkke svfeydlikd krftedkfff hcpitinfks sgankfndei
 901 nlllkekand vhilsidrge rhlayytlvd gkgniikqdt fniigndrmk tnyhdklaai
 961 ekdrdsarkd wkkinnikem kegylsqvvh eiaklvieyn aivvfedlnf gfkrgrfkve
1021 kqvyqklekm lieklnylvf kdnefdktgg vlrayqltap fetfkkmgkq tgiiyyvpag
1081 ftskicpvtg fvnqlypkye svsksqeffs kfdkicynld kgyfefsfdy knfgdkaakg
1141 kwtiasfgsr linfrnsdkn hnwdtrevyp tkelekllkd ysieyghgec ikaaicgesd
1201 kkffakltsv lntilqmrns ktgteldyli spvadvngnf fdsrqapknm pqdadangay
1261 higlkglmll grikknnqegk klnlviknee yfefvqnrnn (SEQ ID NO: 1)
```

FIGURE 9

| Type/ Species | Direct Repeat Sequences of Cpf1 Orthologs (5' – 3') | |
|---|---|---|
| | Processing Sequence | Cpf1 crRNA Sequence |
| FnCpf1 | GUCUAAGAACUUUAAAU (SEQ ID NO: 2) | AAUUUCUACU-GUUGUAGAU (SEQ ID NO: 21) |
| AsCpf1 | GUCAAAAGACCUUUUU (SEQ ID NO: 3) | AAUUUCUACUC-UUGUAGAU (SEQ ID NO: 22) |
| LbCpf1 | GUUUCAAAGAUUAAAU (SEQ ID NO: 4) | AAUUUCUACUAAGUGUAGAU (SEQ ID NO: 23) |
| TsCpf1 | CUCUAGCAGGCCUGGCA (SEQ ID NO: 5) | AAUUUCUACU-GUUGUAGAU (SEQ ID NO: 24) |
| SaCpf1 | AUUUGAAAGCAUCUUUU (SEQ ID NO: 6) | AAUUUCUACU-AUUGUAGAU (SEQ ID NO: 25) |
| Pb2Cpf1 | GGCUAUAAAGCUUAUUU (SEQ ID NO: 7) | AAUUUCUACU-AUUGUAGAU (SEQ ID NO: 26) |
| PgCpf1 | GCCAAAUACCUCUAUAA (SEQ ID NO: 8) | AAUUUCUACU-UUUGUAGAU (SEQ ID NO: 27) |
| MlCpf1 | GUCUAACUACCUUUU (SEQ ID NO: 9) | AAUUUCUACUGUUUGUAGAU (SEQ ID NO: 28) |
| Mb2Cpf1 | GUCUAACUACCUUUU (SEQ ID NO: 10) | AAUUUCUACUGUUUGUAGAU (SEQ ID NO: 29) |
| Mb3Cpf1 | GUCUAACUACCUUUU (SEQ ID NO: 11) | AAUUUCUACUGUUUGUAGAU (SEQ ID NO: 30) |
| Lb4Cpf1 | CUCUAAUAAGAGAUAUG (SEQ ID NO: 12) | AAUUUCUACU-GUUGUAGAU (SEQ ID NO: 31) |
| Lb5Cpf1 | UGCUUAGAACAUUUAAAG (SEQ ID NO: 13) | AAUUUCUACU-AUUGUAGAU (SEQ ID NO: 32) |
| FbCpf1 | GUUUAAAACCACUUUAA (SEQ ID NO: 14) | AAUUUCUACU-AUUGUAGAU (SEQ ID NO: 33) |
| CRbCpf1 | CUCUACAACUGAUAAAG (SEQ ID NO: 15) | AAUUUCUACU-UUUGUAGAU (SEQ ID NO: 34) |
| CPbCpf1 | GUUUAAAAGUCCUAUUG (SEQ ID NO: 16) | GAUUUCUACU-UUUGUAGAU (SEQ ID NO: 35) |
| CMaCpf1 | GUCUAAAACUCAUUCAG (SEQ ID NO: 17) | AAUUUCUACU-AGUGUAGAU (SEQ ID NO: 36) |
| BsCpf1 | UGCUUAGUACUUAUAAAG (SEQ ID NO: 18) | AAUUUCUACU-AUUGUAGAU (SEQ ID NO: 37) |
| BfCpf1 | GCCAAGAACCUAUAGAU (SEQ ID NO: 19) | AAUUUCUACU-GUUGUAGAU (SEQ ID NO: 38) |
| BoCpf1 | GUCUAUAAGACAUUUAU (SEQ ID NO: 20) | AAUUUCUACU-AUUGUAGAU (SEQ ID NO: 39) |

FIGURE 11D
(i)
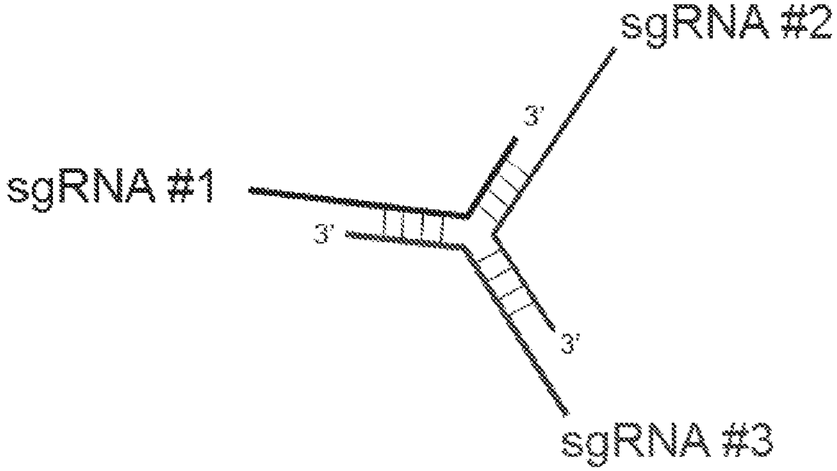
(ii)
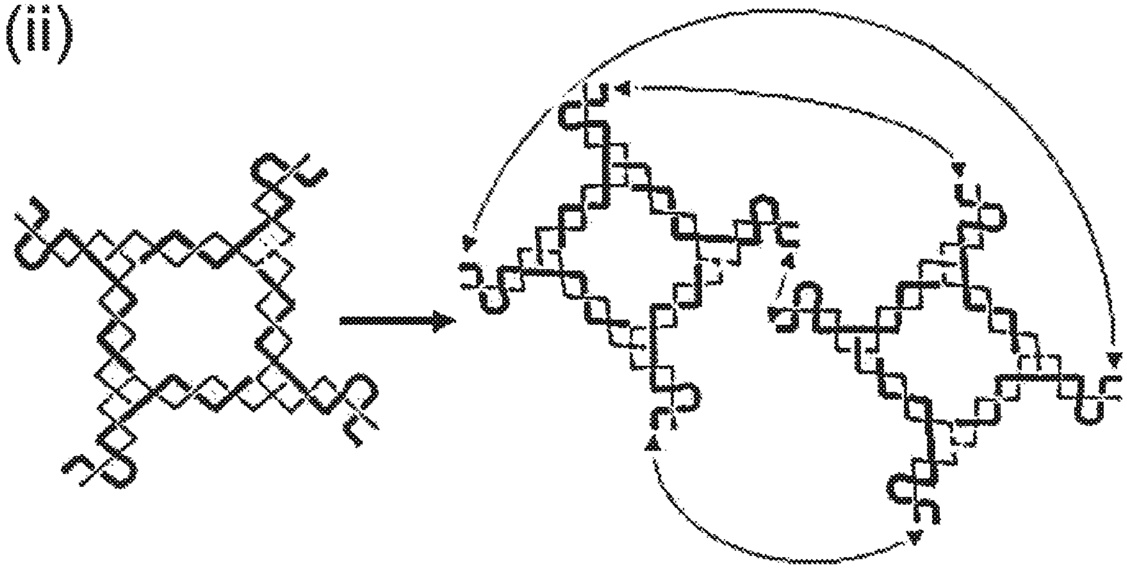

SEQUENCE LISTING

```
<160> NUMBER OF SEQ ID NOS: 39

<210> SEQ ID NO 1
<211> LENGTH: 1300
<212> TYPE: PRT
<213> ORGANISM: Artificial Sequence
<220> FEATURE:
<223> OTHER INFORMATION: Synthetic

<400> SEQUENCE: 1

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240
```

-continued

```
Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Asp Val Lys Ala Ile Lys Asp
        515                 520                 525

Leu Leu Asp Gln Thr Asn Asn Leu Leu His Lys Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
```

-continued

```
            660                 665                 670

Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
    690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
        835                 840                 845

Ile Ala Asn Lys Asn Lys Asp Asn Pro Lys Lys Glu Ser Val Phe Glu
    850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
    930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
            980                 985                 990

Ala Lys Leu Val Ile Glu Tyr Asn  Ala Ile Val Val Phe  Glu Asp Leu
        995                 1000                1005

Asn Phe  Gly Phe Lys Arg Gly  Arg Phe Lys Val Glu  Lys Gln Val
    1010                1015                1020

Tyr Gln  Lys Leu Glu Lys Met  Leu Ile Glu Lys Leu  Asn Tyr Leu
    1025                1030                1035

Val Phe  Lys Asp Asn Glu Phe  Asp Lys Thr Gly Gly  Val Leu Arg
    1040                1045                1050

Ala Tyr  Gln Leu Thr Ala Pro  Phe Glu Thr Phe Lys  Lys Met Gly
    1055                1060                1065

Lys Gln  Thr Gly Ile Ile Tyr  Tyr Val Pro Ala Gly  Phe Thr Ser
    1070                1075                1080
```

```
Lys Ile  Cys Pro Val Thr Gly  Phe Val Asn Gln Leu  Tyr Pro Lys
    1085                 1090                 1095

Tyr Glu  Ser Val Ser Lys Ser  Gln Glu Phe Phe Ser  Lys Phe Asp
    1100                 1105                 1110

Lys Ile  Cys Tyr Asn Leu Asp  Lys Gly Tyr Phe Glu  Phe Ser Phe
    1115                 1120                 1125

Asp Tyr  Lys Asn Phe Gly Asp  Lys Ala Ala Lys Gly  Lys Trp Thr
    1130                 1135                 1140

Ile Ala  Ser Phe Gly Ser Arg  Leu Ile Asn Phe Arg  Asn Ser Asp
    1145                 1150                 1155

Lys Asn  His Asn Trp Asp Thr  Arg Glu Val Tyr Pro  Thr Lys Glu
    1160                 1165                 1170

Leu Glu  Lys Leu Leu Lys Asp  Tyr Ser Ile Glu Tyr  Gly His Gly
    1175                 1180                 1185

Glu Cys  Ile Lys Ala Ala Ile  Cys Gly Glu Ser Asp  Lys Lys Phe
    1190                 1195                 1200

Phe Ala  Lys Leu Thr Ser Val  Leu Asn Thr Ile Leu  Gln Met Arg
    1205                 1210                 1215

Asn Ser  Lys Thr Gly Thr Glu  Leu Asp Tyr Leu Ile  Ser Pro Val
    1220                 1225                 1230

Ala Asp  Val Asn Gly Asn Phe  Phe Asp Ser Arg Gln  Ala Pro Lys
    1235                 1240                 1245

Asn Met  Pro Gln Asp Ala Asp  Ala Asn Gly Ala Tyr  His Ile Gly
    1250                 1255                 1260

Leu Lys  Gly Leu Met Leu Leu  Gly Arg Ile Lys Asn  Asn Gln Glu
    1265                 1270                 1275

Gly Lys  Lys Leu Asn Leu Val  Ile Lys Asn Glu Glu  Tyr Phe Glu
    1280                 1285                 1290

Phe Val  Gln Asn Arg Asn Asn
    1295                 1300
```

<210> SEQ ID NO 2
<211> LENGTH: 17
<212> TYPE: RNA
<213> ORGANISM: Artificial Sequence
<220> FEATURE:
<223> OTHER INFORMATION: Synthetic

<400> SEQUENCE: 2
gucuaagaac uuuaaau 17

<210> SEQ ID NO 3
<211> LENGTH: 16
<212> TYPE: RNA
<213> ORGANISM: Artificial Sequence
<220> FEATURE:
<223> OTHER INFORMATION: Synthetic

<400> SEQUENCE: 3
gucaaaagac cuuuuu 16

<210> SEQ ID NO 4
<211> LENGTH: 16
<212> TYPE: RNA
<213> ORGANISM: Artificial Sequence
<220> FEATURE:
<223> OTHER INFORMATION: Synthetic

<400> SEQUENCE: 4

-continued guuucaaaga uuaaau 16

<210> SEQ ID NO 5
<211> LENGTH: 17
<212> TYPE: RNA
<213> ORGANISM: Artificial Sequence
<220> FEATURE:
<223> OTHER INFORMATION: Synthetic

<400> SEQUENCE: 5
cucuagcagg ccuggca 17

<210> SEQ ID NO 6
<211> LENGTH: 17
<212> TYPE: RNA
<213> ORGANISM: Artificial Sequence
<220> FEATURE:
<223> OTHER INFORMATION: Synthetic

<400> SEQUENCE: 6
auuugaaagc aucuuuu 17

<210> SEQ ID NO 7
<211> LENGTH: 17
<212> TYPE: RNA
<213> ORGANISM: Artificial Sequence
<220> FEATURE:
<223> OTHER INFORMATION: Synthetic

<400> SEQUENCE: 7
ggcuauaaag cuuauuu 17

<210> SEQ ID NO 8
<211> LENGTH: 17
<212> TYPE: RNA
<213> ORGANISM: Artificial Sequence
<220> FEATURE:
<223> OTHER INFORMATION: Synthetic

<400> SEQUENCE: 8
gccaaauacc ucuauaa 17

<210> SEQ ID NO 9
<211> LENGTH: 15
<212> TYPE: RNA
<213> ORGANISM: Artificial Sequence
<220> FEATURE:
<223> OTHER INFORMATION: Synthetic

<400> SEQUENCE: 9
gucuaacuac cuuuu 15

<210> SEQ ID NO 10
<211> LENGTH: 15
<212> TYPE: RNA
<213> ORGANISM: Artificial Sequence
<220> FEATURE:
<223> OTHER INFORMATION: Synthetic

<400> SEQUENCE: 10
gucuaacuac cuuuu 15

<210> SEQ ID NO 11
<211> LENGTH: 15
<212> TYPE: RNA

<213> ORGANISM: Artificial Sequence
<220> FEATURE:
<223> OTHER INFORMATION: Synthetic

<400> SEQUENCE: 11
gucuaacuac cuuuu 15

<210> SEQ ID NO 12
<211> LENGTH: 17
<212> TYPE: RNA
<213> ORGANISM: Artificial Sequence
<220> FEATURE:
<223> OTHER INFORMATION: Synthetic

<400> SEQUENCE: 12
cucuaauaag agauaug 17

<210> SEQ ID NO 13
<211> LENGTH: 18
<212> TYPE: RNA
<213> ORGANISM: Artificial Sequence
<220> FEATURE:
<223> OTHER INFORMATION: Synthetic

<400> SEQUENCE: 13
ugcuuagaac auuuaaag 18

<210> SEQ ID NO 14
<211> LENGTH: 17
<212> TYPE: RNA
<213> ORGANISM: Artificial Sequence
<220> FEATURE:
<223> OTHER INFORMATION: Synthetic

<400> SEQUENCE: 14
guuuaaaacc acuuuaa 17

<210> SEQ ID NO 15
<211> LENGTH: 17
<212> TYPE: RNA
<213> ORGANISM: Artificial Sequence
<220> FEATURE:
<223> OTHER INFORMATION: Synthetic

<400> SEQUENCE: 15
cucuacaacu gauaaag 17

<210> SEQ ID NO 16
<211> LENGTH: 17
<212> TYPE: RNA
<213> ORGANISM: Artificial Sequence
<220> FEATURE:
<223> OTHER INFORMATION: Synthetic

<400> SEQUENCE: 16
guuuaaaagu ccuauug 17

<210> SEQ ID NO 17
<211> LENGTH: 17
<212> TYPE: RNA
<213> ORGANISM: Artificial Sequence
<220> FEATURE:
<223> OTHER INFORMATION: Synthetic

<400> SEQUENCE: 17
gucuaaaacu cauucag 17

<210> SEQ ID NO 18
<211> LENGTH: 18
<212> TYPE: RNA
<213> ORGANISM: Artificial Sequence
<220> FEATURE:
<223> OTHER INFORMATION: Synthetic

<400> SEQUENCE: 18
ugcuuaguac uuauaaag 18

<210> SEQ ID NO 19
<211> LENGTH: 17
<212> TYPE: RNA
<213> ORGANISM: Artificial Sequence
<220> FEATURE:
<223> OTHER INFORMATION: Synthetic

<400> SEQUENCE: 19
gccaagaacc uauagau 17

<210> SEQ ID NO 20
<211> LENGTH: 17
<212> TYPE: RNA
<213> ORGANISM: Artificial Sequence
<220> FEATURE:
<223> OTHER INFORMATION: Synthetic

<400> SEQUENCE: 20
gucuauaaga cauuuau 17

<210> SEQ ID NO 21
<211> LENGTH: 19
<212> TYPE: RNA
<213> ORGANISM: Artificial Sequence
<220> FEATURE:
<223> OTHER INFORMATION: Synthetic

<400> SEQUENCE: 21
aauuucuacu guuguagau 19

<210> SEQ ID NO 22
<211> LENGTH: 19
<212> TYPE: RNA
<213> ORGANISM: Artificial Sequence
<220> FEATURE:
<223> OTHER INFORMATION: Synthetic

<400> SEQUENCE: 22
aauuucuacu cuuguagau 19

<210> SEQ ID NO 23
<211> LENGTH: 20
<212> TYPE: RNA
<213> ORGANISM: Artificial Sequence
<220> FEATURE:
<223> OTHER INFORMATION: Synthetic

<400> SEQUENCE: 23
aauuucuacu aaguguagau 20

<210> SEQ ID NO 24
<211> LENGTH: 19
<212> TYPE: RNA
<213> ORGANISM: Artificial Sequence
<220> FEATURE:

<223> OTHER INFORMATION: Synthetic

<400> SEQUENCE: 24
aauuucuacu guuguagau 19

<210> SEQ ID NO 25
<211> LENGTH: 19
<212> TYPE: RNA
<213> ORGANISM: Artificial Sequence
<220> FEATURE:
<223> OTHER INFORMATION: Synthetic

<400> SEQUENCE: 25
aauuucuacu auuguagau 19

<210> SEQ ID NO 26
<211> LENGTH: 19
<212> TYPE: RNA
<213> ORGANISM: Artificial Sequence
<220> FEATURE:
<223> OTHER INFORMATION: Synthetic

<400> SEQUENCE: 26
aauuucuacu auuguagau 19

<210> SEQ ID NO 27
<211> LENGTH: 19
<212> TYPE: RNA
<213> ORGANISM: Artificial Sequence
<220> FEATURE:
<223> OTHER INFORMATION: Synthetic

<400> SEQUENCE: 27
aauuucuacu uuuguagau 19

<210> SEQ ID NO 28
<211> LENGTH: 20
<212> TYPE: RNA
<213> ORGANISM: Artificial Sequence
<220> FEATURE:
<223> OTHER INFORMATION: Synthetic

<400> SEQUENCE: 28
aauuucuacu guuuguagau 20

<210> SEQ ID NO 29
<211> LENGTH: 20
<212> TYPE: RNA
<213> ORGANISM: Artificial Sequence
<220> FEATURE:
<223> OTHER INFORMATION: Synthetic

<400> SEQUENCE: 29
aauuucuacu guuuguagau 20

<210> SEQ ID NO 30
<211> LENGTH: 20
<212> TYPE: RNA
<213> ORGANISM: Artificial Sequence
<220> FEATURE:
<223> OTHER INFORMATION: Synthetic

<400> SEQUENCE: 30
aauuucuacu guuuguagau 20

<210> SEQ ID NO 31
<211> LENGTH: 19
<212> TYPE: RNA
<213> ORGANISM: Artificial Sequence
<220> FEATURE:
<223> OTHER INFORMATION: Synthetic

<400> SEQUENCE: 31
aauuucuacu guuguagau 19

<210> SEQ ID NO 32
<211> LENGTH: 19
<212> TYPE: RNA
<213> ORGANISM: Artificial Sequence
<220> FEATURE:
<223> OTHER INFORMATION: Synthetic

<400> SEQUENCE: 32
aauuucuacu auuguagau 19

<210> SEQ ID NO 33
<211> LENGTH: 19
<212> TYPE: RNA
<213> ORGANISM: Artificial Sequence
<220> FEATURE:
<223> OTHER INFORMATION: Synthetic

<400> SEQUENCE: 33
aauuucuacu auuguagau 19

<210> SEQ ID NO 34
<211> LENGTH: 19
<212> TYPE: RNA
<213> ORGANISM: Artificial Sequence
<220> FEATURE:
<223> OTHER INFORMATION: Synthetic

<400> SEQUENCE: 34
aauuucuacu uuuguagau 19

<210> SEQ ID NO 35
<211> LENGTH: 19
<212> TYPE: RNA
<213> ORGANISM: Artificial Sequence
<220> FEATURE:
<223> OTHER INFORMATION: Synthetic

<400> SEQUENCE: 35
gauuucuacu uuuguagau 19

<210> SEQ ID NO 36
<211> LENGTH: 19
<212> TYPE: RNA
<213> ORGANISM: Artificial Sequence
<220> FEATURE:
<223> OTHER INFORMATION: Synthetic

<400> SEQUENCE: 36
aauuucuacu aguguagau 19

<210> SEQ ID NO 37
<211> LENGTH: 19
<212> TYPE: RNA
<213> ORGANISM: Artificial Sequence
<220> FEATURE:
<223> OTHER INFORMATION: Synthetic -continued

```
<400> SEQUENCE: 37

aauuucuacu auuguagau                                                  19


<210> SEQ ID NO 38
<211> LENGTH: 19
<212> TYPE: RNA
<213> ORGANISM: Artificial Sequence
<220> FEATURE:
<223> OTHER INFORMATION: Synthetic

<400> SEQUENCE: 38

aauuucuacu guuguagau                                                  19


<210> SEQ ID NO 39
<211> LENGTH: 19
<212> TYPE: RNA
<213> ORGANISM: Artificial Sequence
<220> FEATURE:
<223> OTHER INFORMATION: Synthetic

<400> SEQUENCE: 39

aauuucuacu auuguagau                                                  19
```

MODIFIED CPF1 GUIDE RNA

CROSS-REFERENCE TO RELATED APPLICATIONS

This patent application is the national stage of International Patent Application PCT/US2018/054027 filed on Oct. 2, 2018; which claims priority to U.S. Provisional Patent Application No. 62/567,123, filed on Oct. 2, 2017; U.S. Provisional Patent Application No. 62/617,138, filed on Jan. 12, 2018; and U.S. Provisional Application No. 62/697,327, file on Jul. 12, 2018, the entire disclosures of which are hereby incorporated by referenced.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 1,800 Byte ASCII (Text) file name "512701_ST25.TXT," created on Oct. 23, 2018.

BACKGROUND OF THE INVENTION

RNA-guided endonucleases have proven to be an effective tool for genome engineering in multiple cell types and microorganisms. RNA-guided endonucleases generate site-specific double-stranded DNA breaks or single-stranded DNA breaks within target nucleic acids. When the cleavage of a target nucleic acid occurs within a cell, the break in the nucleic acid can be repaired by non-homologous end joining (NHEJ) or homology directed repair (HDR).

Direct delivery of RNA-guided endonucleases and their gene-editing components (e.g., guide RNA) into cells both in vitro and in vivo has tremendous potential as a therapeutic strategy for treating genetic diseases. Currently, however, direct delivery of these components into cells with reasonable efficiency is challenging.

Therefore, there is a need to identify new compositions and related methods to improve cellular delivery and other properties of RNA-guided endonucleases that will enhance genome engineering. This invention provides such compositions and related methods.

BRIEF SUMMARY OF THE INVENTION

The invention is a nucleic acid comprising of a Cpf1 crRNA with an extension sequence. In one aspect, the nucleic acid comprises a Cpf1 crRNA and an extension sequence on the 5' end of the Cpf1 crRNA, wherein the extension sequence comprises fewer than about 60 nucleotides. In another aspect, the nucleic acid comprises a Cpf1 crRNA, a processing sequence 5' of the Cpf1 crRNA, and an extension sequence 5' of the processing sequence. Also provided is a composition comprising the nucleic acid, a carrier, and optionally a Cpf1 protein or vector encoding the protein.

The invention also provides a method for genetically modifying a eukaryotic target cell. The method involves contacting the eukaryotic target cell with the nucleic acid containing the Cpf1 crRNA as described herein.

These and other aspects of the invention are described in greater detail in the following sections.

BRIEF DESCRIPTION OF THE SEVERAL VIEWS OF THE DRAWING(S)

Figure 2:
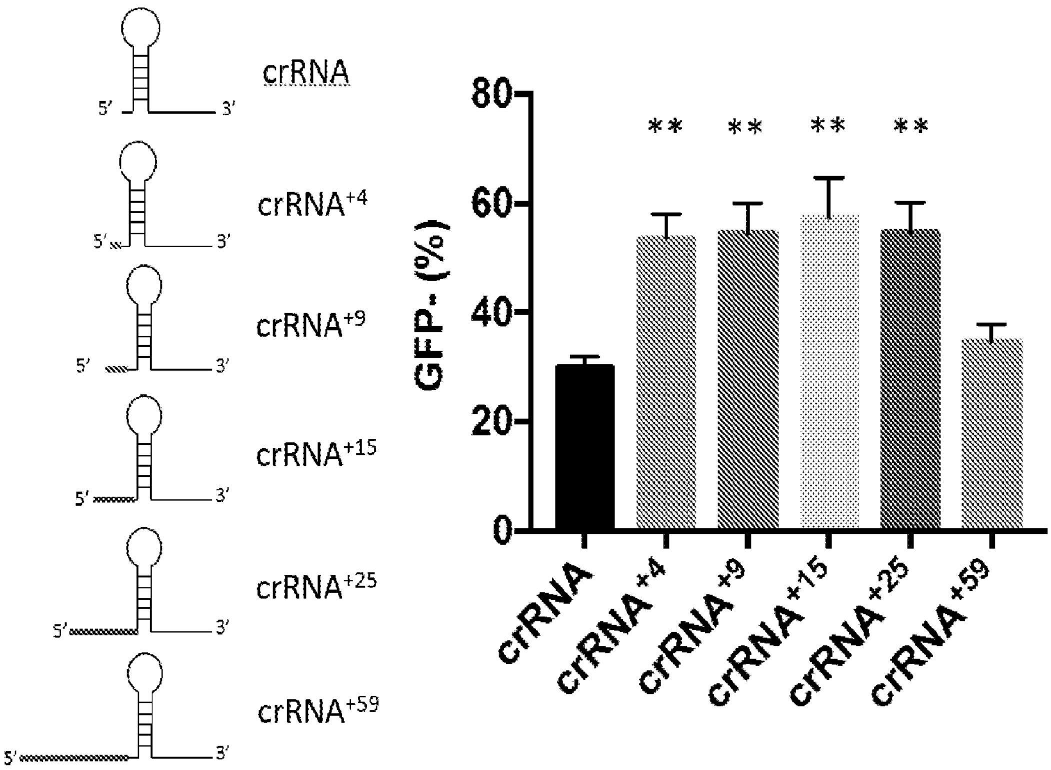

FIG. 2 provides a graph (right panel) illustrating gene editing efficiency as a function of GFP knockdown for 5' extended crRNA delivered to GFP-HEK cells via electroporation, and a schematic illustration of the crRNA (left panel).

Figure 3A:
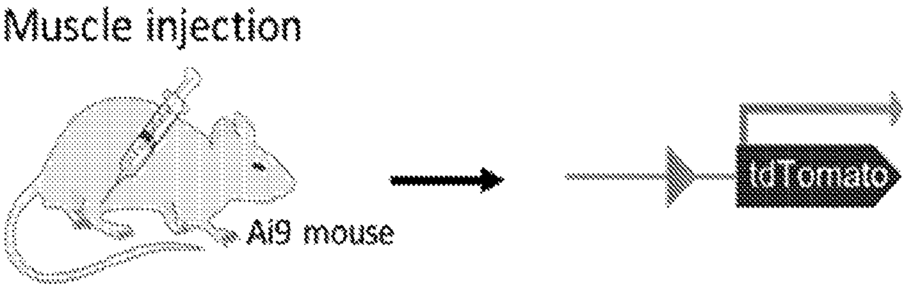

FIG. 3A is a schematic illustration of in vivo studies in AI9 mice.

Figure 3B:
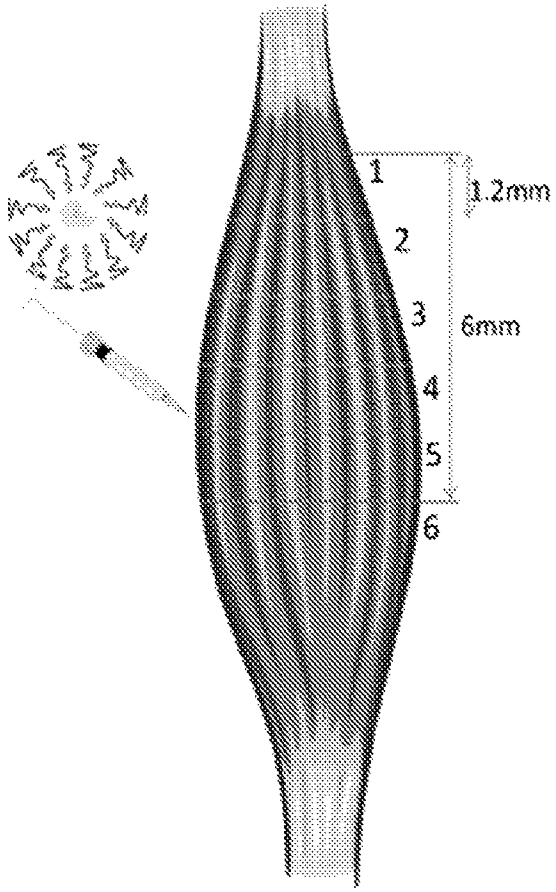

FIG. 3B is a schematic illustration of gastroenemius muscle injection site and imaging sections.

Figure 4A:
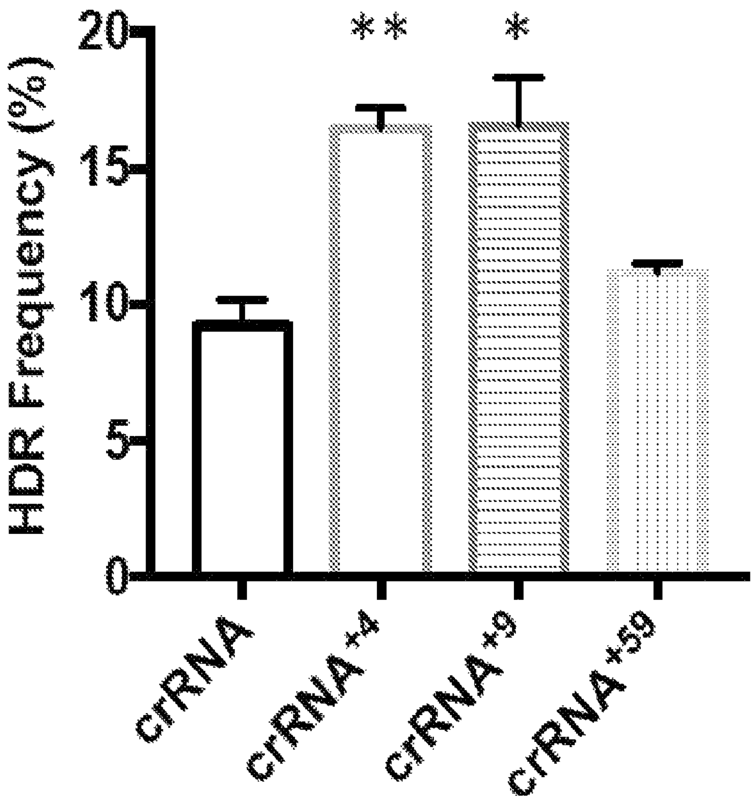

FIG. 4A is a graph of HDR frequency for crRNA with different extensions delivered with donor DNA using electroporation.

Figure 4B:
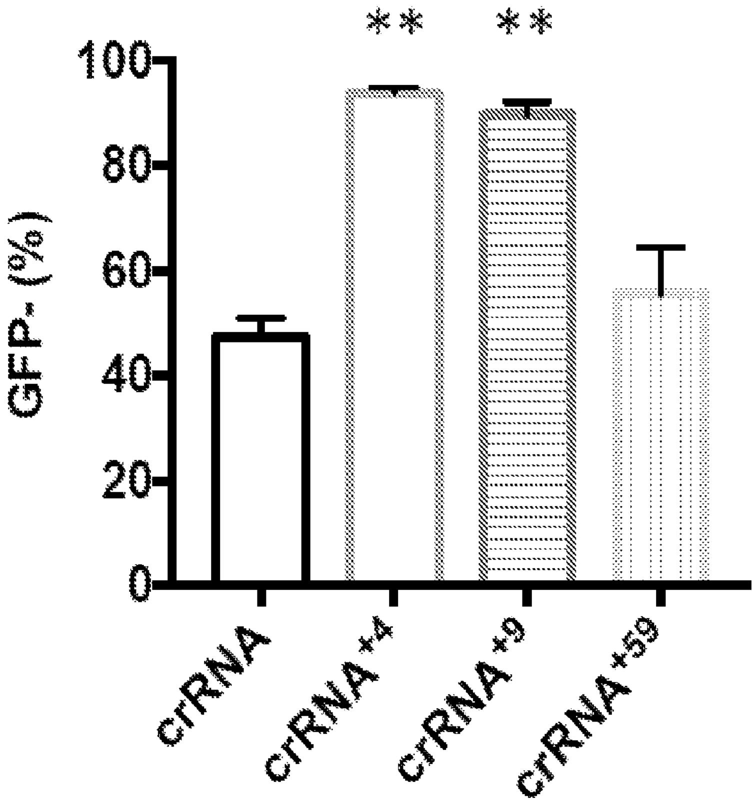

FIG. 4B is a graph of percentage of GFP− cells for crRNA with different extensions delivered with donor DNA, illustrating NHEJ efficiency using electroporation.

Figure 4C:
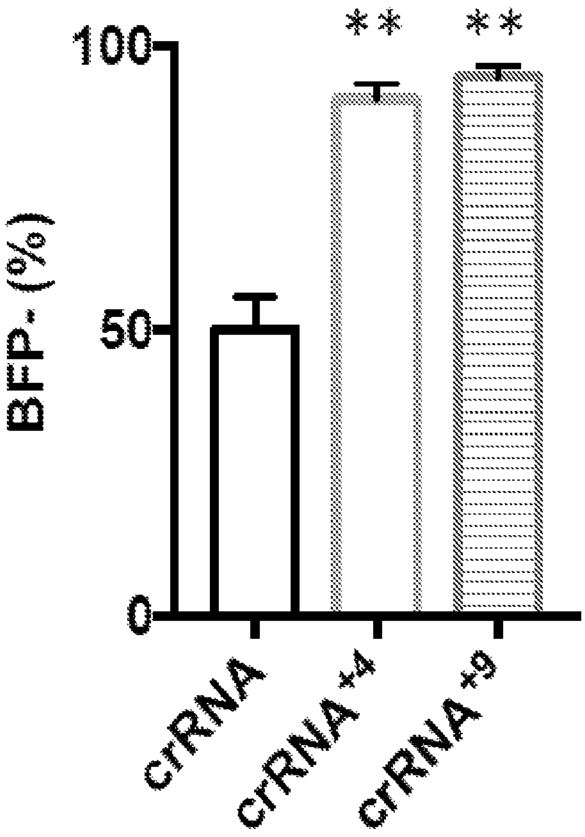

FIG. 4C is a graph of percentage of BFP− cells for crRNA with different extensions delivered with donor DNA, illustrating NHEJ efficiency using electroporation.

Figure 4D:
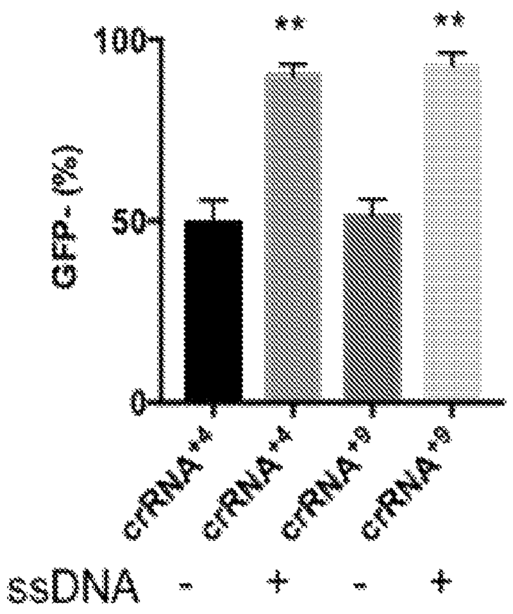

FIG. 4D is a graph of percentage of GFP− cells for extended crRNA delivered with and without single-stranded DNA (ssDNA) without homology to the target sequence using electroporation.

Figure 4E:
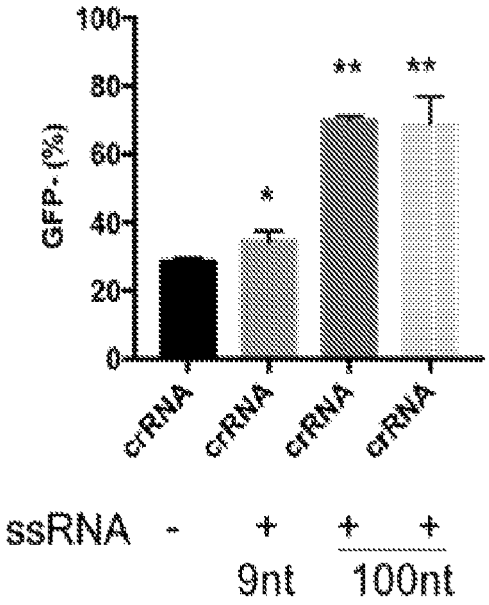

FIG. 4E is a graph illustrating gene editing as a percentage GFP− cells for crRNA extended with 100 nt RNAs and 9nt RNAs without homology for the target sequence using electroporation.

Figure 4F:
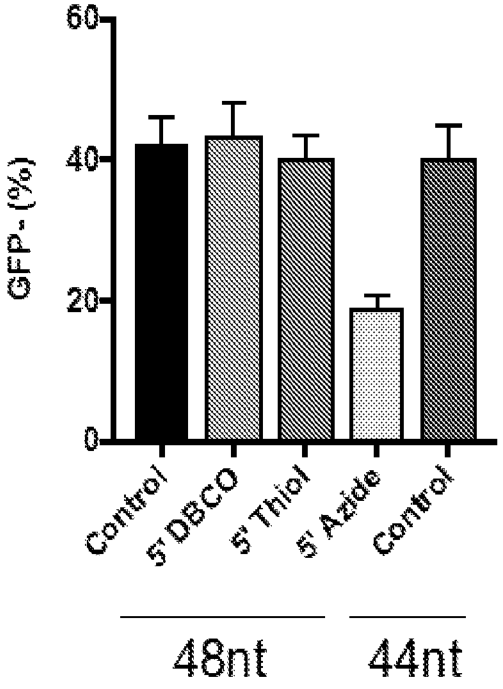

FIG. 4F is a graph of percentage of GFP− cells for crRNA with and without a 4 nt extension and further modified with a chemical moiety using electroporation.

Figure 5B:
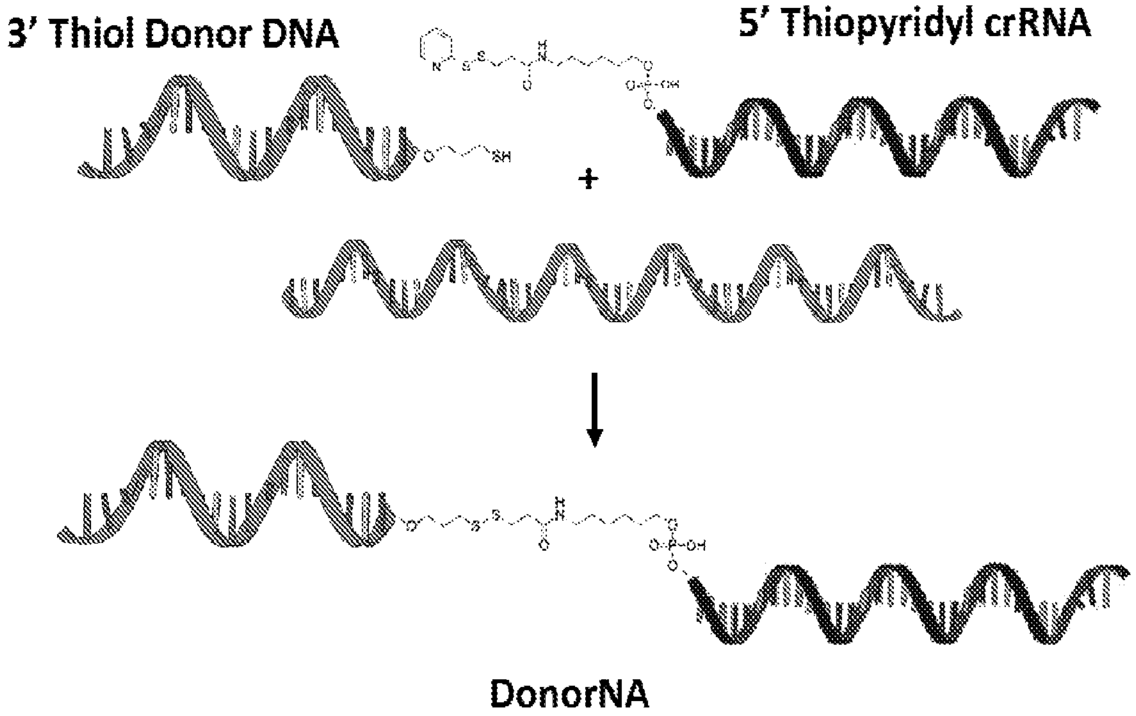

FIGS. 5A and 5B provide schematic illustrations of conjugating crRNA and donor DNA.

Figure 5C:
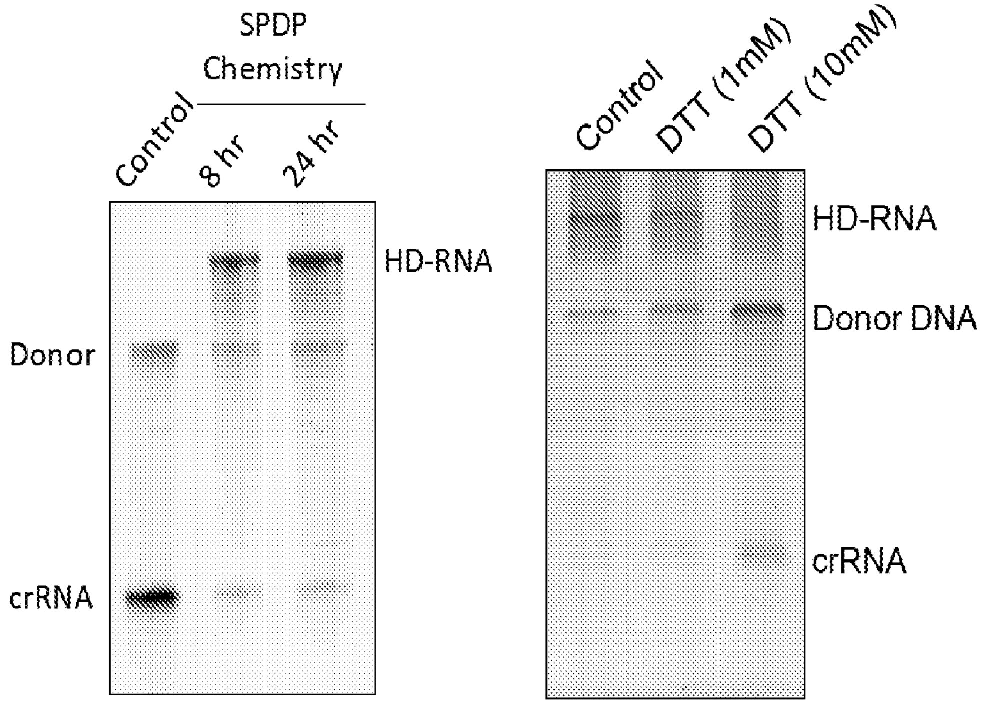

FIG. 5C are images of gel electrophoretic separations illustrating the release of donor DNA and crRNA from a conjugated crRNA/DNA molecule after reduction with thiols.

Figure 6:
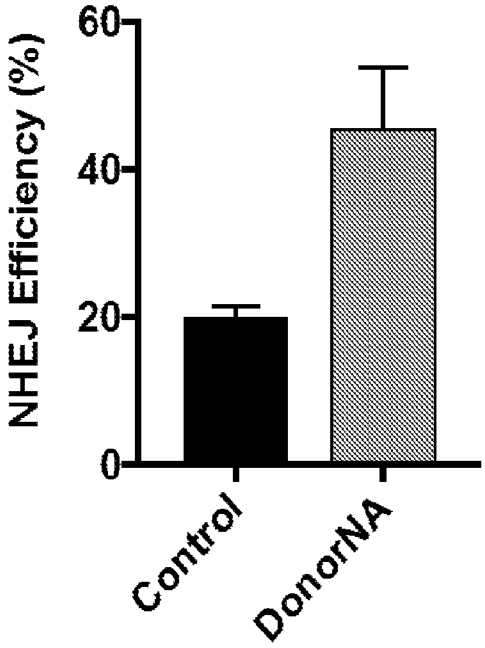

FIG. 6 is a graph demonstrating that Cpf1 conjugated to IID-RNA induces NHEJ in GFP-HEK cells after transfection with a PAsp(DET) (i.e., cationic polymer).

Figure 7:
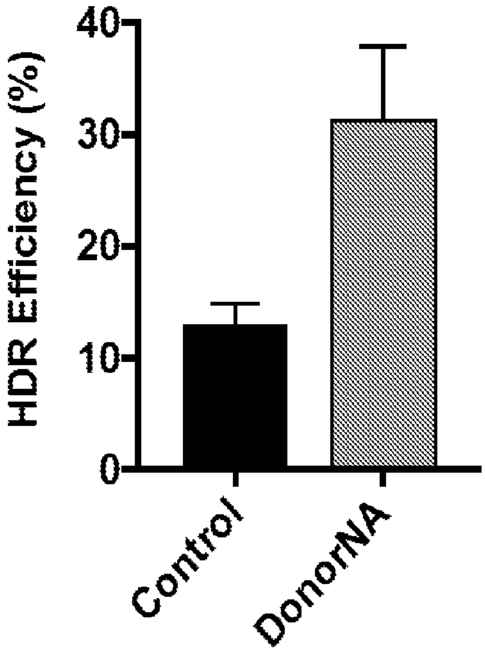

FIG. 7 is a graph demonstrating that Cpf1 conjugated to HD-RNA induces HDR in GFP-HEK cells after transfection with a PAsp(DET) (i.e., cationic polymer).

FIG. 8 provides the sequence of a Cpf1 protein.

FIG. 9 provides examples of Cpf1 processing sequences.

Figure 10A:
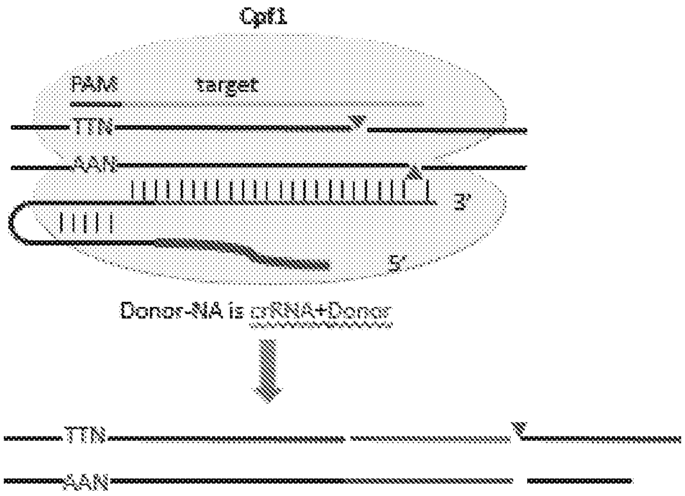

FIG. 10A shows a schematic illustration of crRNA conjugated to donor DNA.

Figure 10B:

FIG. 10B illustrates the sequences used in a crRNA conjugated to donor DNA.

Figure 10C:
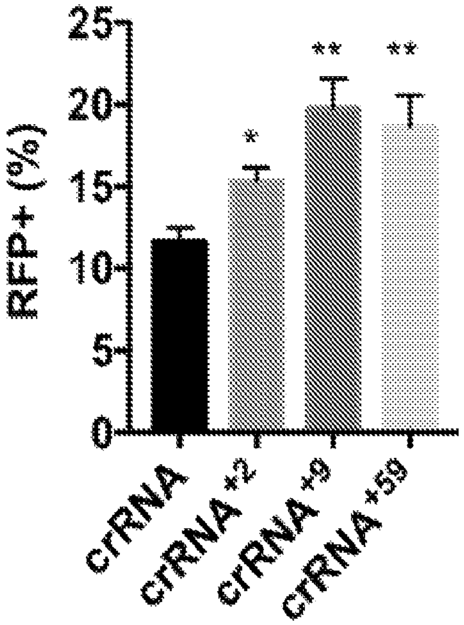

FIG. 10C is a graph of percentage of RFP+ cells after treatment with various crRNA and Cpf1 using electroporation in primary Ai9 myoblasts.

Figure 10D:
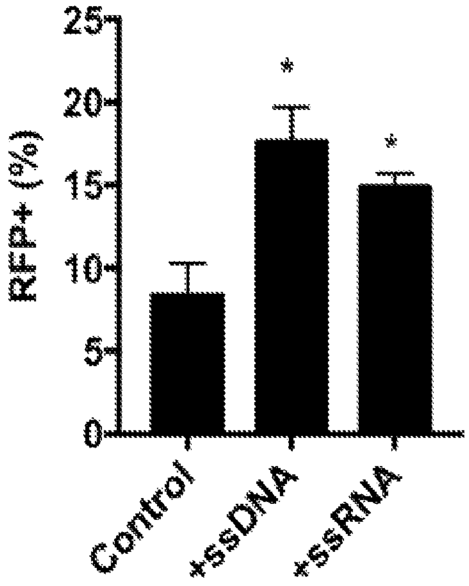

FIG. 10D is a graph of percentage of RFP− cells transfected with 100 nt DNA or RNA into primary Ai9 myoblasts.

Figure 10E:
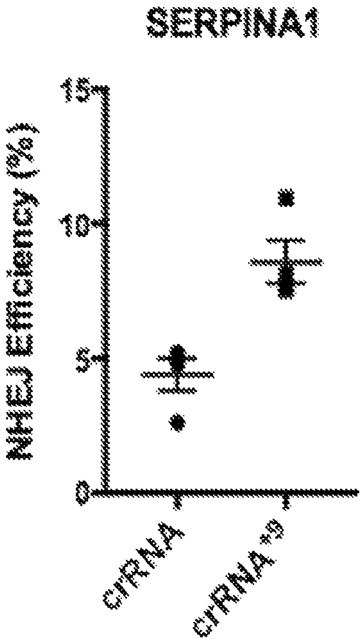

FIG. 10E is a graph of NHEJ efficiency in HepG2 cells transfected with Cpf1 RNP with or without 9 nt extension on crRNA targeting Serpina1 gene using electroporation.

Figure 11A:
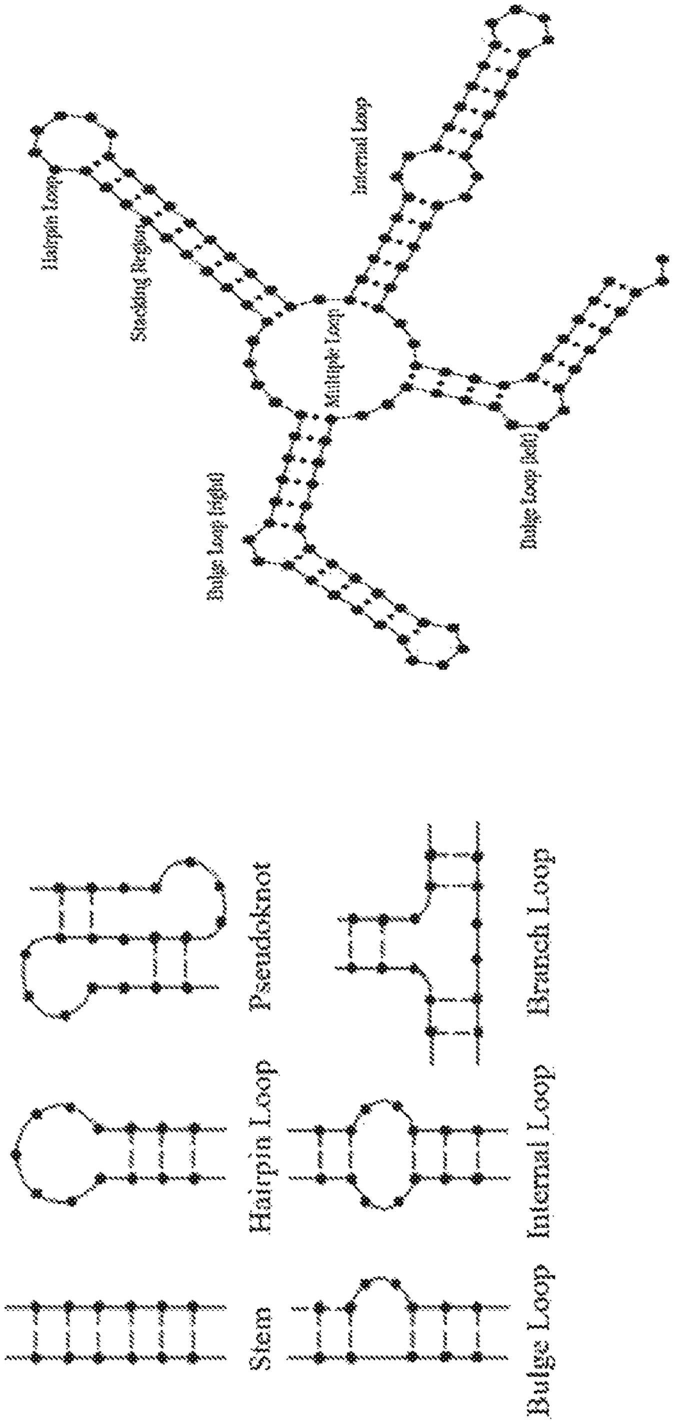

FIG. 11A illustrates RNA structures that can be used in crRNA extensions.

Figure 11B:
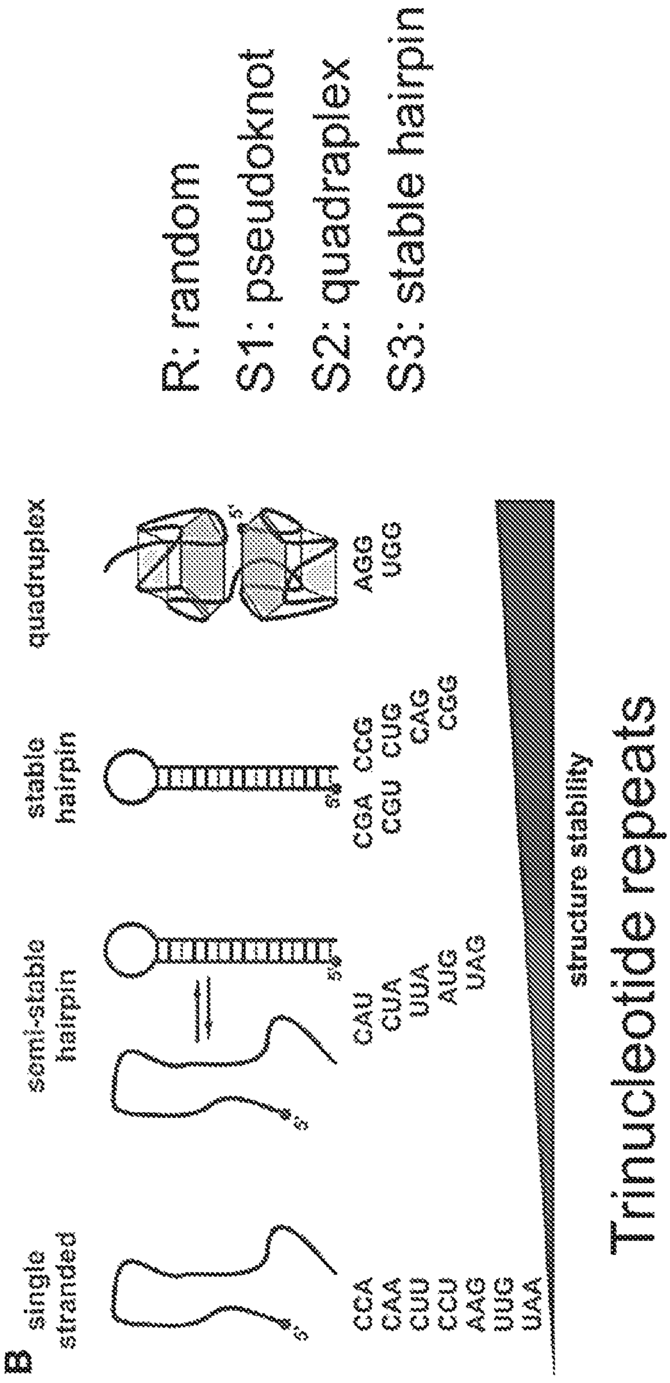

FIG. 11B illustrates trinucleotide repeats that can be used to provide various RNA structures.

Figure 11C:
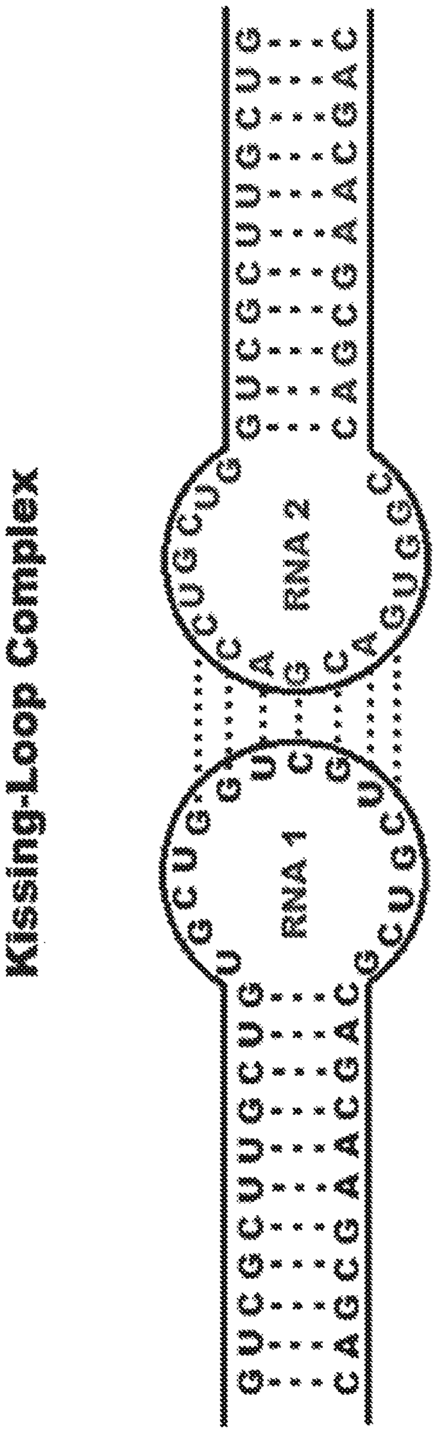

FIG. 11C illustrates the intersection of hybridizing extension sequences of crRNA in a kissing loop, which can be used to form crRNA multimers.

FIG. 11D illustrates the intersection of hybridizing extension sequences of crRNA to form trimers (panel (i)) or octamers (panel (ii)).

Figure 12:
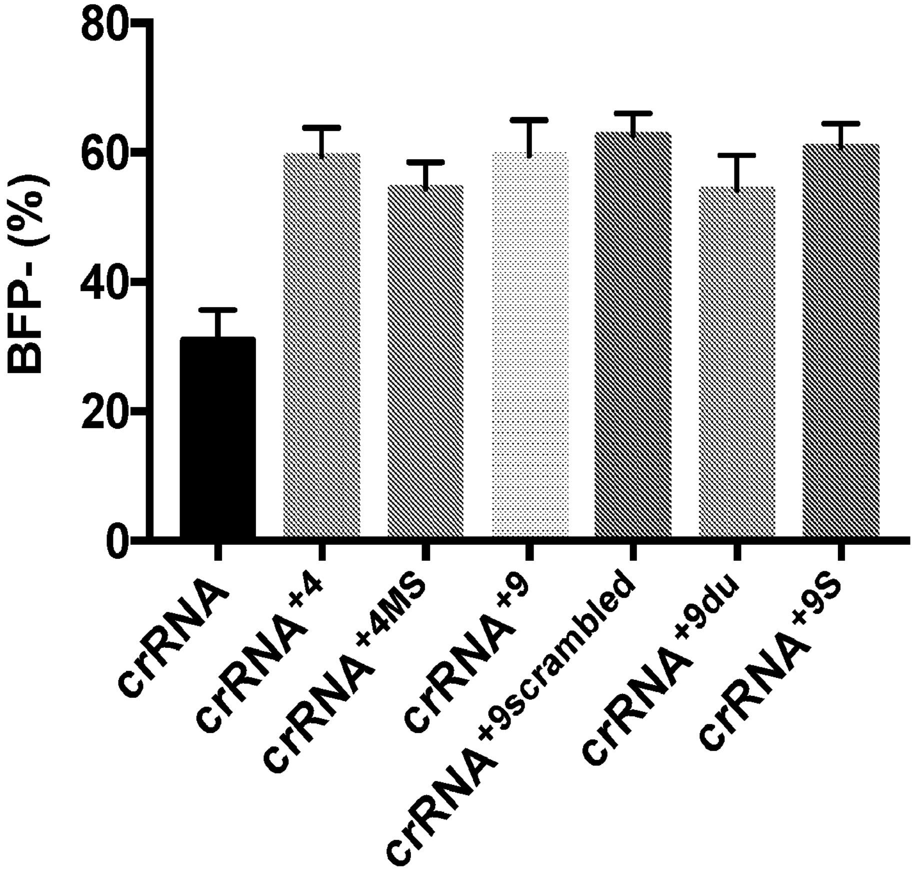

FIG. 12 shows the editing efficiency (% BPF−) of various Cpf1 crRNAs in BFP expressing HEK293T cells. MS is 2'-OMe 3'-phosphorothioate modifications on the first three nucleotides from 5' end, +9du is 2'-deoxy modification on the $9^{th}$ nucleotide from the 5' end, +9S is phosphorothioate modifications on the first 9 nucleotides from 5'end. BFP knock-out efficiency was measured with flow cytometry 7 days after electroporation. Mean±S.E, n=3. All extended crRNAs show statistically significant difference to unmodified crRNA with p value smaller than 0.05 by student-t-test.

Figure 13A:
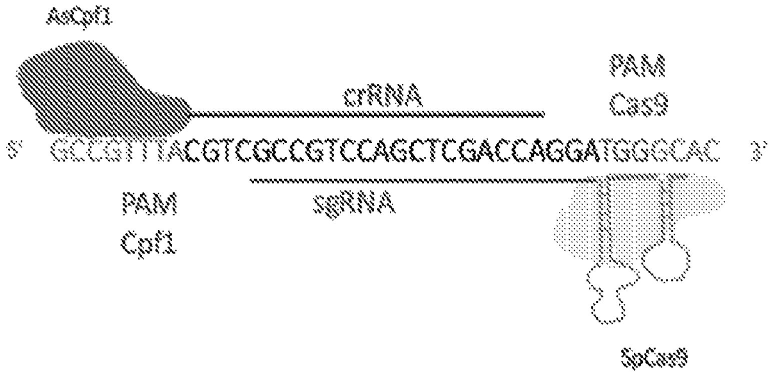

FIG. 13A is an illustration of unmodified Cas9 sgRNA and Cpf1 crRNA; and

Figure 13B:
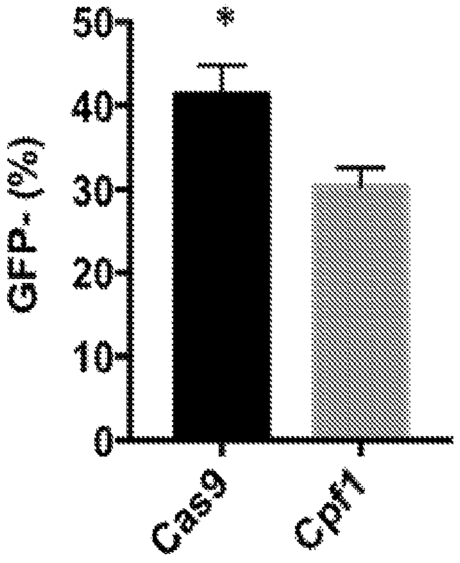
Figure 13C:
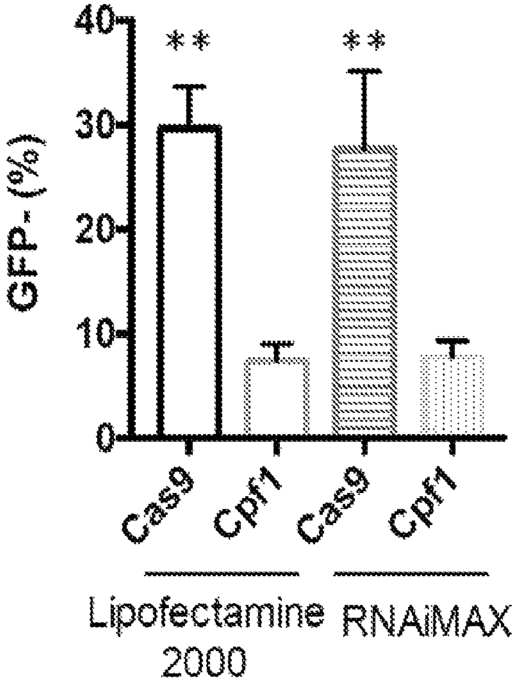

FIGS. 13B and 13C are graphs showing relative activity of Cas9 sgRNA and Cpf1 crRNA as a function of GFP knockdown.

Figure 14:
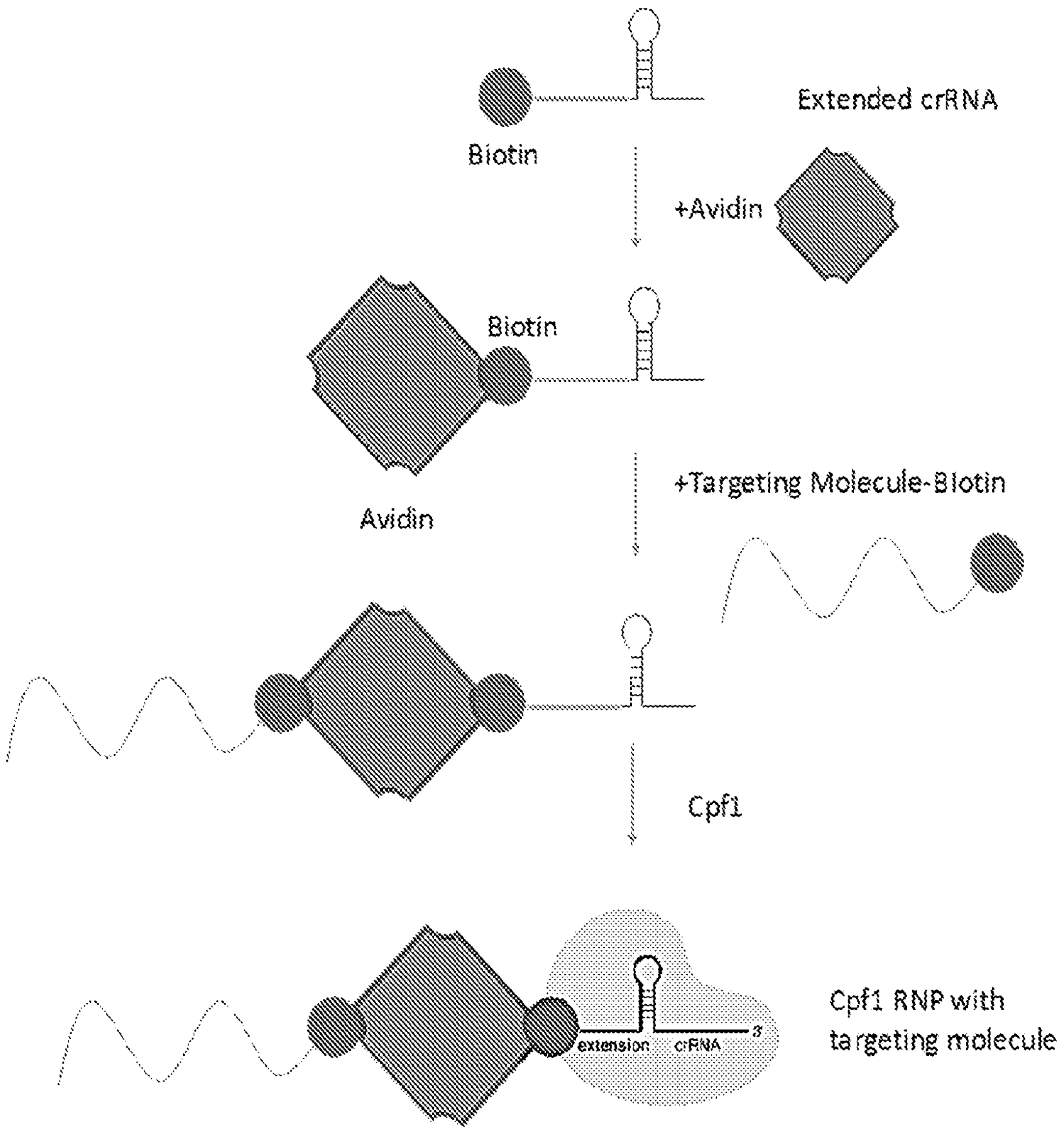

FIG. 14 is a schematic illustration of an extended crRNA modified with biotin and avidin and linked to a targeting molecule comprising biotin.

Figure 15A:
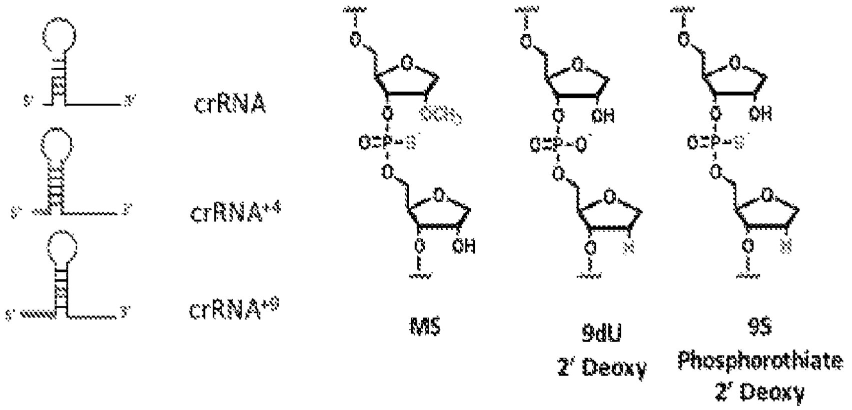

FIG. 15A is a schematic illustration of chemical modifications made to crRNAs with extension.

Figure 15B:
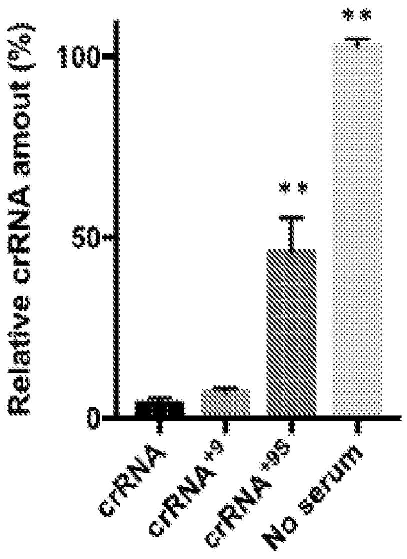

FIG. 15B is a graph quantifying the remaining crRNA amount after incubation in serum.

Figure 15C:
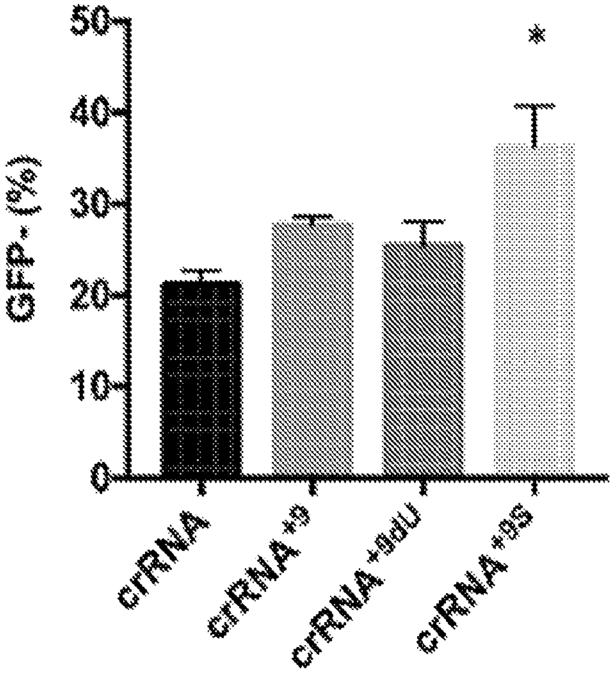

FIG. 15C is a graph of percentage GFP− cells after delivery of crRNA with 9nt extension and chemical modification using lipofectamine.

Figure 15D:
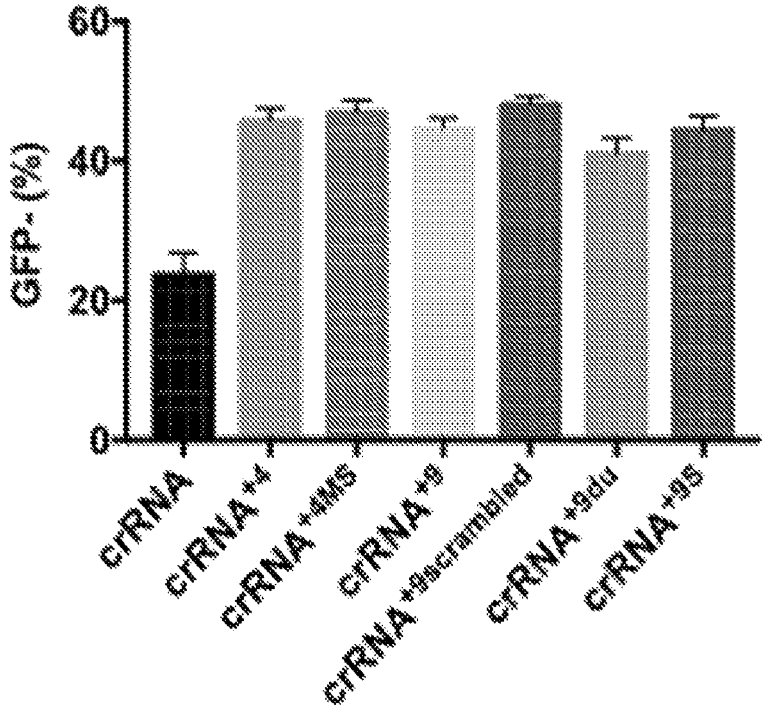

FIG. 15D is a graph comparing the percentage GFP− cells after delivery of extended crRNA with chemical modifications and unmodified extended crRNA together with Cpf1 using electroporation.

Figure 16:
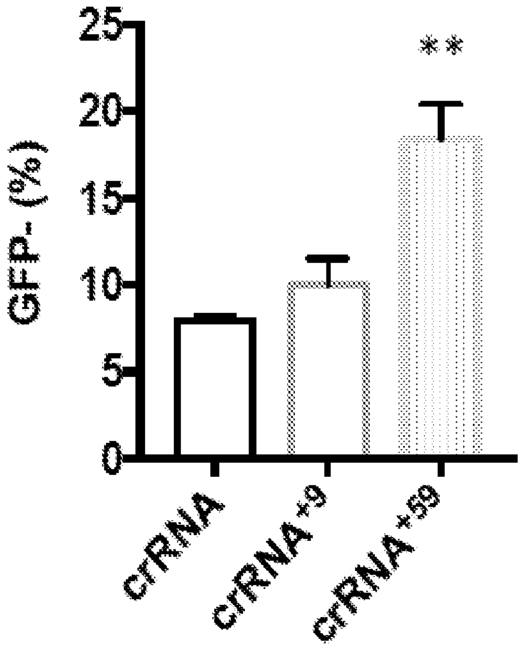

FIG. 16 is a graph comparing the cationic polymer mediated delivery and NHEJ generation of Cpf1-crRNA complexes comprising unmodified crRNA (41nt), 9 base pair extended crRNA (50nt total), or 59 base pair extended crRNA (100nt total).

Figure 17:
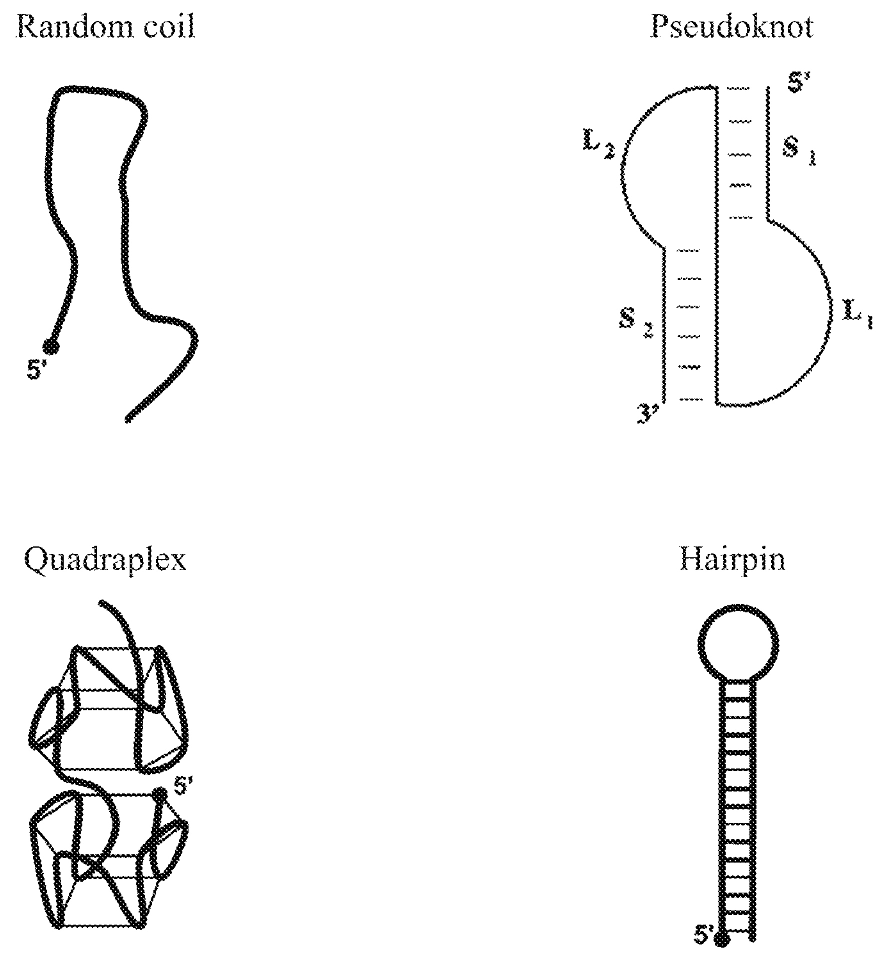

FIG. 17 is a set of drawings showing the random coil, pseudoknot, quadraplex, and hairpin structures of representative RNA extended sequences, such as those shown in Table 1.

DETAILED DESCRIPTION OF THE INVENTION

The invention provides modified guide nucleic acid for Cpf1, referred to as a "crRNA," with enhanced properties as compared to conventional crRNA molecules. crRNA, as used herein, refers to a nucleic acid sequence (e.g., RNA) that binds to the RNA-guided endonuclease Cpf1 and targets the RNA-guided endonuclease to a specific location within a target nucleic acid to be cleaved by Cpf1. Cpf1 is an RNA-guided endonuclease of a class II CRISPR/Cas system that is involved in type V adaptive immunity. Cpf1 does not require a tracrRNA molecule like other CRISPR enzymes, and requires only a single crRNA molecule to function. Cpf1 prefers a "TTN" PAM motif that is located 5' upstream of its target. In addition, the cut sites for Cpf1 are staggered by about 3-5 bases, which create "sticky ends" (Kim et al., 2016. "Genome-wide analysis reveals specificities of Cpf1 endonucleases in human cells" published online Jun. 6, 2016). These sticky ends with 3-5 bp overhangs are thought to facilitate NHEJ-mediated-ligation, and improve gene editing of DNA fragments with matching ends.

Persons skilled in the art will appreciate that the Cpf1 crRNA can be from any species or any synthetic or naturally occurring variant or orthologue derived or isolated from any source. That is to say that the Cpf1 crRNA can have the required elements (e.g., sequence or structure) of a crRNA that is recognized (bound by) any Cpf1 polypeptide or ortholog from any species of bacteria, or synthetic variants thereof. Examples of Cpf1 crRNA sequences are provided in FIG. 9; thus, for instance, examples of Cpf1 crRNA include those comprising any of SEQ ID NOs: 21-39). An example of a Cpf1 crRNA sequence of a synthetic variant Cpf1 is the crRNA corresponding to the MAD7 Cpf1 orthologue by Inscripta, Inc. (CO, USA). Another example of a Cpf1 variant is a Cpf1 modified to reduce or eliminate RNAse activity, such as by introducing a modification at H800A, K809A, K860A, F864A, and R790A of *Acidaminococcus* Cpf1 (AsCpf1) or corresponding position of a different Cpf1 ortholog (e.g., H800A mutation or H→A mutation at corresponding position).

Typically, crRNA comprises a targeting domain and a stem loop domain located 5' of the targeting domain. The overall length of the crRNA is not particularly limited so long as it can guide Cpf1 to a specific location within the target nucleic acid. The stem-loop domain generally is about 19-22 nucleotides (nt) in length, and the targeting/guide domain is anywhere from about 14-25 nt (e.g., at least about 14nt, 15nt, 16nt, 17nt, or 18nt). The overall length of the Cpf1 crRNA can, in some embodiments, have a length of from 20 to 100 nt, from 20 nt to 90 nt, from 20 nt to 80 nt, from 20 nt to 70 nt, from 20 nt to 60 nt, from 20 nt to 55 nt, from 20 nt to 50 nt, from 20 nt to 45 nt, from 20 nt to 40 nt, from 20 nt to 35 nt, from 20 nt to 30 nt, or from 20 nt to 25 nt.

One aspect of the disclosure provides a nucleic acid comprising a Cpf1 crRNA, an extension sequence 5' of the crRNA, and, optionally, a processing sequence, which may be positioned between the crRNA and the extension sequence, within the extension sequence, or 5' of the extension sequence.

Extension Sequence

The nucleic acid of the invention comprises an extension sequence positioned 5' of the crRNA. The extension sequence may comprise any combination of nucleic acids (i.e., any sequence). In an embodiment, the extension sequence increases the overall negative charge density of the nucleic acid molecule, and improves delivery of the nucleic acid including the crRNA.

In some embodiments, the extension sequence can be cleaved once in the cell. Without wishing to be bound by any particular theory or mechanism of action, it is believed that Cpf1 can cleave the extension sequence. However, in certain applications, it is desirable to use a construct in which the extension sequence is not cleaved from the Cpf1 crRNA. Thus, in some embodiments, the extension sequence is not cleavable by the Cpf1 crRNA. For instance, the extension sequence or some portion or region thereof can comprise one or more modified internucleotide linkages (modified "backbone") that are resistant to cleavage by Cpf1 crRNA (e.g., nuclease resistant). Examples of modified internucleotide linkages include, without limitation, phosphorothioate, phosphorodithioate, methylphosphonate, phosphoramidate, 2'-O-methyl, 2'-O-methoxyethyl, 2'-fluoro, bridged nucleic acid (BNA), or phosphotriester modified bonds, as well as combinations thereof. The extension sequence or some portion thereof also can comprise synthetic nucleotides, such as xeno nucleic acids (XNAs) that are resistant to nucleases. XNAs are nucleic acids in which the ribofuranose ring of DNA or RNA is replaced by five- or six-membered modified ribose molecules, such as 1,5 anhydrohexitol nucleic acids (HNAs), cyclohexenyl nucleic acids (CeNAs), and 2'4'-C—(N-methylaminomethylene) bridged nucleic acids (BNAs), 2'-O,4'-C-methylene-β-D-ribonucleic acids or locked nucleic acids (LNAs), ANA (arabinonucleic acids), 2'-fluoro-arabinonucleic acid (FANAs) and α-L-threofuranosyl nucleic acids (TNAs). Furthermore, any combination thereof also can be used.

The length of the extension sequence is not particularly limited so long as the extension sequence increases the overall negative charge density. For example, the extension sequence can have a length of at least about 2 nucleotides (nt) up to about 1000 nt (e.g., at least about 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, or 900, and up to about 1000 nt). In one aspect, the extension sequence is no more than about 100 nucleotides in length, such as no more than about 80 nucleotides in length, no more than about 60 nucleotides in length, or no more than about 40 nucleotides in length (e.g., no more than about 30 nucleotides in length or no more than about 20 nucleotides in length). Any of the foregoing lower and upper limits on length can be expressed as ranges. Shorter sequences also can be used (e.g., no more than about 15 nucleotides, or no more than about 10 nucleotides). In some embodiments, the extension sequence comprises at least about 2 nucleotides, such as at least about 4 nucleotides, at least about 6 nucleotides, or even at least about 9 nucleotides. Any of the foregoing can be expressed as a range. Thus, for instance, the extension sequence can be about 2-60 nucleotides (e.g., about 2-40 nucleotides, about 2-30 nucleotides, about 2-20 nucleotides, about 2-15 nucleotides, or about 2-10 nucleotides), about 4-60 nucleotides (e.g., about 4-40 nucleotides, about 4-30 nucleotides, about 4-20 nucleotides, about 4-15 nucleotides, or about 4-10 nucleotides); about 6-60 nucleotides (e.g., about 6-40 nucleotides, about 6-30 nucleotides, about 6-20 nucleotides, about 6-15 nucleotides, or about 6-10 nucleotides); or about 9-60 nucleotides (e.g., about 9-40 nucleotides, about 9-30 nucleotides, about 9-20 nucleotides, about 9-15 nucleotides, or about 9-10 nucleotides).

In some embodiments, the extension sequence has no function other than imparting greater overall negative charge density to the nucleic acid construct. In this embodiment, for instance, the extension sequence is a random or non-coding sequence. In some instances, such as when a processing sequence is used, the sequence can be degraded upon cleavage of the processing sequence and release from the nucleic acid construct.

In other embodiments, the extension sequence has a function separate and apart from imparting greater overall negative charge density to the nucleic acid construct. The extension sequence can have any additional function. For instance, the extension sequence can provide a hybridization site for another nucleic acid, such as a donor nucleic acid. Also, in some embodiments, the extension sequence can be an aptamer and/or promote cell binding. However, it is sometimes not desirable to recruit binding of proteins other than the RNA-guided endonuclease to the guide RNA. Furthermore, aptamer sequences typically have complex folding patterns that can be bulky and not compact. Thus, in other embodiments, the extension sequence is not an aptamer sequence.

In some embodiments, the extension sequence can comprise a sequence encoding a protein the expression of which is desired in the target cell to be edited. For instance, the extension sequence could comprise a sequence encoding a RNA-guided endonuclease, such as the RNA-guided endonuclease that is paired with (i.e., recognizes and is guided by) the crRNA that is used in the nucleic acid construct. The extension sequence can comprise, for instance, the sequence of the mRNA of the RNA-guided endonuclease.

In some embodiments, the extension self-folds (self-hybridizes) to provide a structured extension. There is no limitation on the type of structure provided. The extension can have a random coil structure; however, in some embodiments, the extension has a structure that is more compact than a random coil structure of the same number of nucleotides, which provides a greater negative charge density. By increasing the overall length of the extension, the negative charge of the molecule is increased. When a more compact structure is used, the overall negative charge density of the molecule is further increased. Compactness or charge density can be determined according to mobility in gel electrophoresis. More particularly, if gel electrophoresis is performed for two nucleic acids with the same number of nucleotides run together on the same gel, the nucleic acid with the higher mobility (moves farthest in the gel) is deemed to have a more compact structure.

In another embodiment, the extension sequence comprises at least one semi-stable hairpin structure, stable hairpin structure, pseudoknot structure, G-quadraplex structure, bulge loop structure, internal loop structure, branch loop structure, or a combination thereof. These types of nucleotide structures are known in the art and schematically illustrated in FIG. 11A. It is to be understood that the illustrations are merely for the purpose of illustrating the general structure, and is not intended to be a detailed illustration of the actual molecular structure. Those of skill in the art recognize that a hairpin structure, for instance, can have interspersed regions of non-complementarity that produce "bulges" or other variations in the structure, and that the other depicted structures can include similar variations. The structure of a given nucleotide sequence can be determined using available algorithms (e.g., "The mfold Web Server" operated by Rensselaer Polytechnic Institute and The RNA Institute, College of Arts and Sciences, State University of New York at Albany; see also M. Zuker, D. H. Mathews & D. H. Turner. Algorithms and Thermodynamics for RNA Secondary Structure Prediction: A Practical Guide In *RNA Biochemistry and Biotechnology,* 11-43, J. Barciszewski and B. F. C. Clark, eds., NATO ASI Series, Kluwer Academic Publishers, Dordrecht, NL, (1999)).

The type of structure provided can be controlled using a repeating trinucleotide motif (e.g., FIG. 11B). A repeating trinucleotide motif is a motif of three nucleotides that is repeated in the sequence at least twice (e.g., repeated two or more times, three or more times, four or more times, five or more times, six or more times, seven or more times, eight or more times, or ten or more times). Thus, the extension sequence can comprise a repeating trinucleotide motif. In one embodiment, the extension sequence comprises a repeating trinucleotide motif of CAA, UUG, AAG, CUU, CCU, CCA, UAA, or a combination thereof, which provides a random coil sequence. In another embodiment, the extension sequence comprises a repeating trinucleotide motif of CAU, CUA, UUA, AUG, UAG, or a combination thereof, which provides a semi-stable hairpin structure. In another embodiment, the extension sequence comprises a repeating CNG trinucleotide motif (e.g., CGG, CAG, CUG, CCG), a repeating trinucleotide motif of CGA or CGU, or a combination thereof, which provides a stable hairpin structure. In another embodiment, the extension sequence comprises a repeating trinucleotide motif of AGG, UGG, or combination thereof, which provides a quadruplex (or G-quadruplex) structure. In yet another embodiment, the extension sequence comprises a combination of the foregoing trinucleotide motifs and a combination of the different structures thereby produced. For instance, the extension sequence could have a region comprising a random coil structure, a region comprising a semi-stable hairpin, a region comprising a stable hairpin, and/or a region comprising a quadruplex. Each region might, thus, comprise the repeating trinucleotide motif associated with the indicated structure. Non-limiting examples of structures are presented in FIG. 17 and the below table:

TABLE 1

Representative RNA extended sequences (35 nucleotides) and their corresponding structures.

| | Sequences (5'→3') |
|---|---|
| Random coil | R1: UCCCGAGCUGUGCUUCGUUUCUACACUUGUACAUG |
| | R2: CCCUGCGACAGUCAUCUCGGCCGCCAAAGACACAG |
| | R3: UUCGUCGCCUUGGGCCGUCGUUUUUCGCUCGUGGG |
| Pseudoknot | S1: UUGGCGCAGUGGGCUAGCGCCACUCAAAAGGCCCA |
| Quadraplex | S2: UUAGGAGGAGGAGGAGGAGGAGGAGGAGGAGGAGG |
| Hairpin | S3: UUCGUCGUCGUCGUCGUCGUCGUCGUCGUCGUCGU |
| | S4: UUCUGCUGCUGCUGCUGCUGCUGCUGCUGCUGCUG |

The extension sequence also can be used to create crRNA multimers; thus, in another embodiment, there is provided a crRNA multimer comprising two or more crRNA molecules (e.g., 3 or more, 4 or more, 5 or more, 6 or more, 7 or more, or even 8 or more crRNA molecules), wherein each crRNA comprises an extension sequence as described herein, and the crRNA molecules of the multimer are joined by their extension sequences, for instance, through base pairing or hybridization. Thus, in one embodiment, each crRNA of the multimer comprises an extension sequence comprising a region sufficiently complimentary to a region of an extension of another crRNA of the multimer to facilitate hybridization. The complimentary region can be of any suitable length to facilitate the interaction (e.g., 4 nt or more, 6 nt or more, 8 nt or more, 10 nt or more, 15 nt or more, etc.). crRNA multimers are useful, for example, to deliver multiple crRNAs simultaneously, such as when multiple crRNAs are desired for particular therapeutic strategies. One example of such a use is exon skipping, in which a DNA fragment is cleaved by two crRNAs to restore the functional reading frame (e.g., Ousterout D G, et al. (2015), Multiplex CRISPR/Cas9-based genome editing for correction of dystrophin mutations that cause Duchenne Muscular Dystrophy. *Nat Commun.* 6:6244). Exon skipping requires two crRNAs each targeting a different site (one at the 5'-site and the other at the 3'-site) in the nucleus for targeting. Ideally, the ratio of two crRNAs should be 1 to 1; however, it is difficult to maintain this ratio. By pairing crRNAs (e.g., each comprising different targeting sequences) in multimers through appropriate extension structures, delivery in the desired ratio can be facilitated.

In one embodiment, two or more crRNAs with structured extensions engage in an RNA "kissing" interaction (a.k.a. loop-loop interaction), which occurs when the unpaired nucleotides in one structured extension sequence (e.g., a hairpin loop) base pair with the unpaired nucleotides in another structure (e.g., another hairpin loop) on a second crRNA. An example of this type of interaction is illustrated FIG. 11C. The formation of kissing loops or other structures multimerizes the two or more crRNA molecules. This strategy can be applied to link several crRNA molecules.

Hybridization of complementary sequences in the extension on each crRNA also can be used to facilitate multimerization. For instance, supermolecular crRNA structures can be constructed via the extended regions that have capability of self-assembly. For example, a trimer can be formed by three RNA molecules with appropriately placed hybridization regions (e.g., FIG. 11D, panel (i); Shu D, Shu Y, Haque F, Abdelmawla S, & Guo P (2011) Thermodynamically stable RNA three-way junctions as platform for constructing multi-functional nanoparticles for delivery of therapeutics. *Nat Nanotechnol.* 6(10):658-667.)). Similarly, a RNA octamer could be generated by assembling sixteen RNA molecules (FIG. 11D, panel (ii); Yu J, Liu Z, Jiang W, Wang G, & Mao C (2014) De novo design of an RNA tile that self-assembles into a homo-octameric nanoprism. *Nat Commun.* 6:5724)).

Any of the foregoing types of extensions can be used with or without a processing sequence. In some embodiments, the nucleic acid can include multiple processing sequences and extension sequences. For instance, the nucleic acid can further comprise a second processing sequence 5' of the first extension sequence and a second extension sequence 5' of the second processing sequence. The second processing and extension sequences can be the same as the first processing and extension sequences (e.g., repeats), or either or both of the second processing sequence and second extension sequence can be different from the first processing sequence and/or extension sequence. The nucleic acid is not particularly limited to any number of processing and extension sequences, and can have 2, 3, 4, 5, etc. processing and/or extension sequences.

The 5' terminus of the nucleic acid construct (i.e., the processing sequence or extension sequence, as applicable, at the 5' terminus) can be further modified as desired. For instance, the 5' terminus can be modified with a functional group, such as a functional group that participates in bioorthogonal or "click" chemistry reactions. For example, the 5' end of the nucleic acid can be chemically modified with an azide, a tetrazine, alkyne, strained alkene, or strained alkyne. Such a modification can facilitate joining a desired chemical moiety or molecule to the construct using appropriately paired functional group.

The 5' terminus of the nucleic acid can be modified to comprise a biofunctional molecule, optionally via the bioorthogonal or "click" chemistry described above. The biofunctional molecule can be any molecule that enhances the delivery or activity of the RNA-guided endonuclease, or provides some other desired function, such as targeting the nucleic acid to a particular destination (e.g., a moiety that targets a particular protein, cell receptor, tissue, etc.) or facilitating the tracking of the construct (e.g., a detectable label, such as fluorescent marker, radiolabel, or the like). Examples of biofunctional molecules include, for instance, endosomolytic polymers, donor DNA molecules, amino sugars (e.g., N-acetylgalatosamine (GalNAc) or tri-Gal- NAc) guide and/or tracer RNA (e.g., single guide RNA), as well as other peptides, nucleic acids, and targeting ligands (e.g., antibodies, ligands, cell receptors, aptamers, galactose, sugars, small molecules). In one embodiment, the crRNA comprises a biotin or avidin (or streptavidin) molecule conjugated to the crRNA extension, allowing the modified crRNA to bind to another molecule (e.g., targeting molecule or peptide) conjugated with avidin/streptavidin or biotin as appropriate (see, e.g., FIG. 14). In another embodiment, the crRNA extension can be covalently linked to an amino sugar in any suitable manner, such as by a linker. As used herein "amino sugar" is a sugar molecule in which a hydroxyl group has been replaced with an amine group (e.g., galactosamine) and/or a nitrogen that is a part of a complex functional group (e.g., N-acetylgalactosamine (GalNAc); tri-N-acetylgalactosamine (triantennary N-acetylgalactosamine)). The amino sugar can be modified to contain an optional spacer group. Examples of amino sugars include N-acetylgalactosamine (GalNAc), trivalent GalNAc, or triantennary N-acetylgalactosamine. An example of an amino sugar group includes the following:

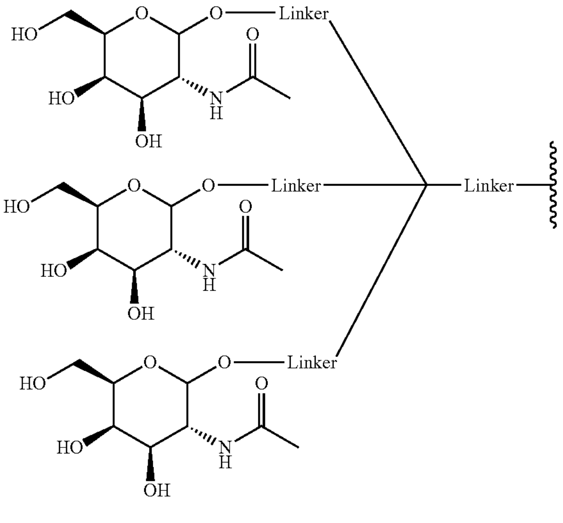

wherein the linker can be any commonly known in the art, and each can be the same or different from the others. Generally, the linker is a saturated or unsaturated aliphatic or heteroaliphatic chain. The aliphatic or heteroaliphatic chain typically comprises 1-30 members (e.g., 1-30 carbon, nitrogen, and/or oxygen atoms), and can be substituted with one or more functional groups (e.g., one or more ketone, ether, ester, amide, alcohol, amine, urea, thiourea, sulfoxide, sulfone, sulfonamide, and/or disulfide groups). In some instances, a shorter aliphatic or heteroaliphatic chain is used (e.g., about 1-15 members, about 1-10 members, about 1-5 members, about 3-15 members, about 3-10 members, about 5-15 members, or about 5-10 members in the chain). In other instances, a longer aliphatic or heteroaliphatic chain is used (e.g., about 5-30 members, about 5-25 members, about 5-20 members, about 10-30 members, about 10-25 members, about 10-20 members, about 15-30 members, about 15-25 members, or about 15-20 members in the chain). Examples of spacer groups include substituted and unsubstituted alkyl, alkenyl, and polyethylene glycol (e.g., PEG 1-10 or PEG 1-5), or a combination thereof. A more specific example provided for illustration is as follows:

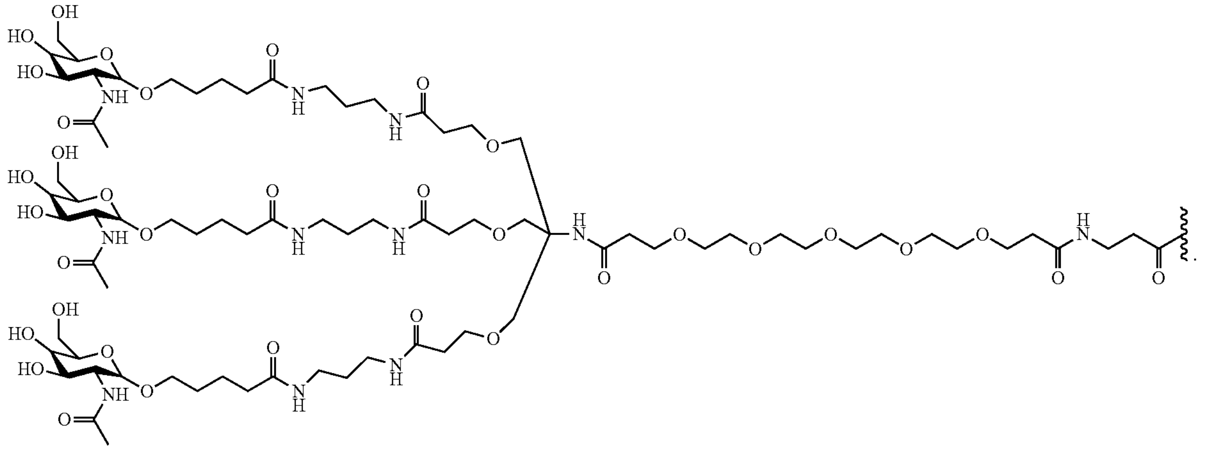

Prior to conjugation with the linker, the amino sugar can comprise a functional group (e.g., azide, tetrazine, alkyne, strained alkene, or strained alkyne), which allows conjugation to an appropriately paired functional group attached to the crRNA extension (e.g., at the 5' terminus). Thus, for instance, the amino sugar prior to conjugation with the extended crRNA can comprise:

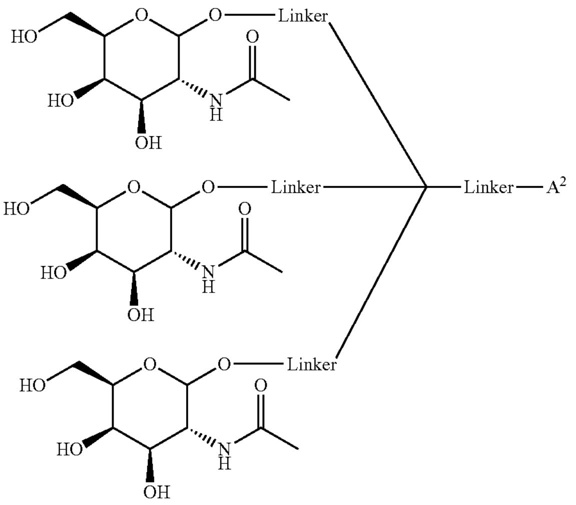

wherein $A^2$ comprises azide, tetrazine, alkyne, strained alkene, or strained alkyne, as described herein. A more specific example is as follows:

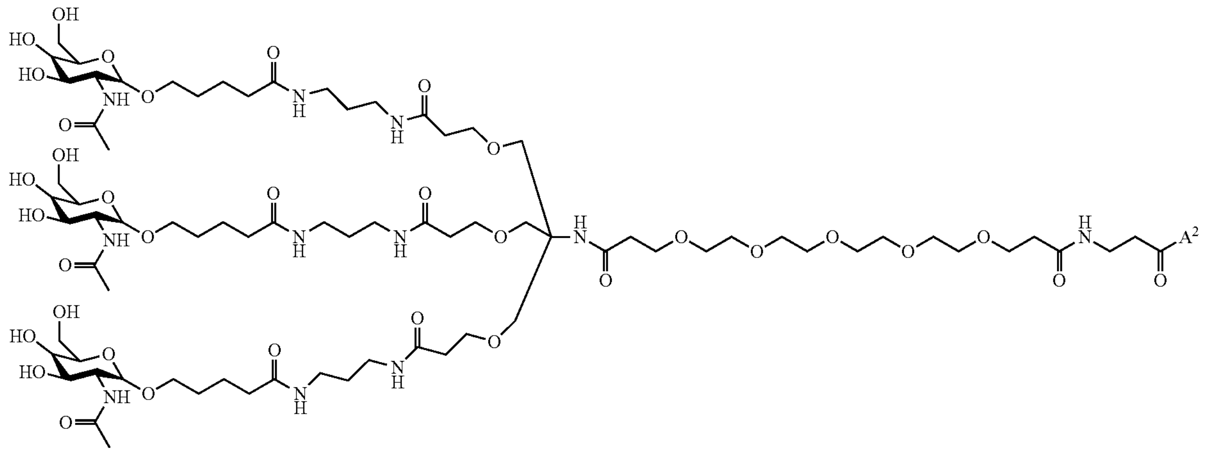

wherein $A^2$ comprises azide, tetrazine, alkyne, strained alkene, or strained alkyne, as described herein, e.g.:

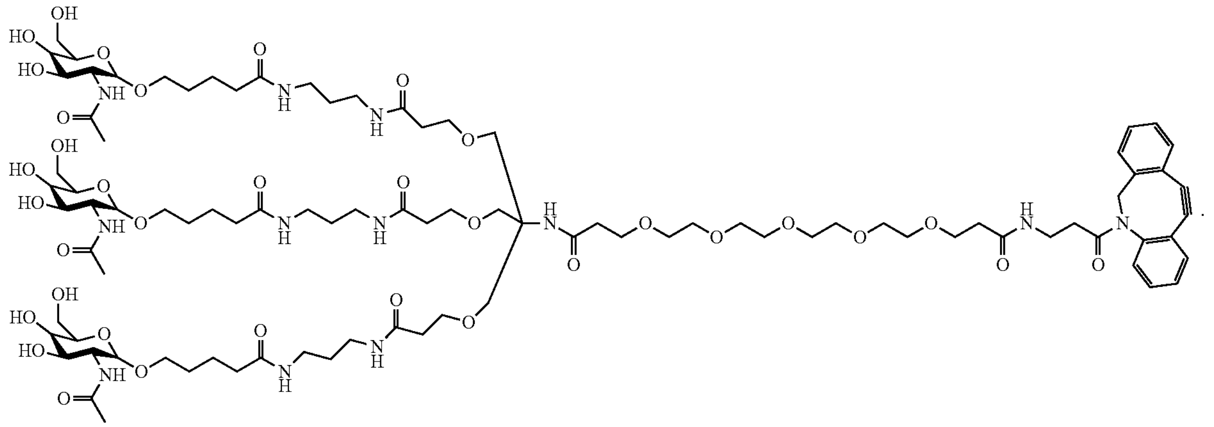

Processing Sequence

In some embodiments, the crRNA comprises a processing sequence. The processing sequence is a nucleic acid sequence that is self-cleaved in vitro or in vivo by Cpf1 without the need for a guide/targeting sequence. Without wishing to be bound by any particular theory or mechanism of action, it is believed that the processing sequence when present is cleaved upon entry into the cell, and the crRNA is released from any extension sequence. The processing sequence can be positioned between the crRNA and the extension sequence. In this configuration, upon cleavage of the processing sequence, the crRNA is released from the extension sequence of the nucleic acid construct provided herein.

The processing sequence also could be located within the extension sequence, positioned 5' of the extension sequence, or could serve as the extension sequence. Also, multiple processing sequences could be used. For instance, a second processing sequence could serve as an extension sequence, alone or together with additional nucleotide sequences. However, the extension sequence generally will be different from the processing sequence when present. Furthermore, in one embodiment, the extension sequence does not comprise the processing sequence and/or any other whole (complete) crRNA sequence.

In some embodiments, the processing sequence is positioned immediately 5' of the crRNA (i.e., directly attached to the crRNA sequence). In other embodiments, a spacer sequence can be present between the crRNA and the processing sequence. The spacer sequence can be of any length (e.g., 1, 2, 3, 4, 5, 6, 7, 8, 9, or 10 nt) provided it does not prevent Cpf1 cleavage of the processing sequence or the function of the released crRNA after cleavage.

In one embodiment, the processing sequence comprises a fragment of a direct repeat sequence of a Cpf1 array. Cpf1 arrays (also sometimes referred to as pre-crRNA) are naturally occurring arrays comprising a direct-repeat sequence and a spacer sequence between each direct repeat. The direct repeat portion of the array comprises two parts: a crRNA sequence portion and a processing portion. Within a given direct repeat, the processing portion is positioned 5' of the crRNA sequence portion, often immediately 5' of the processing portion. According to this embodiment, the processing sequence of the nucleic acid provided herein comprises at least a fragment of the processing portion of the direct repeat sufficient to effect Cpf1 cleavage. For instance, the processing sequence can comprise a fragment of at least 5 contiguous nucleotides of the processing portion of the direct repeat sequence, such as at least 6, 7, 8, 9, 10, 11, 12, 13, 14, 15, 16, or 17 nt of the processing portion of the direct repeat sequence (or the entire processing portion of the direct repeat sequence), the length of which will depend on the species from which the direct repeat originates. In some embodiments, the processing sequence comprises the entire processing portion of the direct repeat sequence. The direct repeat can be from a Cpf1 array of any microorganism. Examples of direct repeat sequences, and processing portions of direct repeat sequences, are provided in FIG. 9. The processing sequence of the inventive nucleic acid can comprise a fragment or entire sequence of any of the processing sequences in FIG. 9 (e.g., SEQ ID NOs: 2-20).

Donor Nucleic Acid

The nucleic acid construct provided herein can further comprise a donor nucleic acid (also referred to as a donor polynucleotide). The donor polynucleotide is a nucleic acid that is inserted at the cleavage site induced by the RNA-guided endonuclease (e.g., Cpf1). The nucleic acid of the donor polynucleotide can be any type of nucleic acid known in the art. For example, the nucleic acid can be DNA, RNA, DNA/RNA hybrids, artificial nucleic acid or any combination thereof. In one embodiment the nucleic acid of the donor polynucleotide is DNA, also known herein as "donor DNA."

The donor polynucleotide is typically single-stranded, and serves as a template for the creation of double stranded DNA containing a desired sequence. The donor polynucleotide will contain sufficient identity (e.g., 85%, 90%, 95%, or 100% sequence identity) to a genomic sequence flanking the cleavage site to a region of the genomic sequence near the cleavage site (e.g., within about 50 bases or less, within about 30 bases or less, within about 15 bases or less, or within about 10 bases or less, within about 5 bases or less, or immediately adjacent the cleavage site) to support homology directed repair between the donor sequence and the genomic sequences flanking the cleavage site to which the donor sequence bears sufficient sequence identity. Donor polynucleotide sequences can be of any length, but must have a sufficient number of nucleotides bearing sequence identity on both sides of the cleavage site to facilitate HDR. These regions of the donor polynucleotide are known as homology arms. The homology arms can be have the same number of bases or a different number of bases, and each are generally be at least 5 nucleotides in length (e.g., 10 nucleotides or more, 15 nucleotides or more, 20 nucleotides or more, 50 nucleotides or more, 100 nucleotides or more, 150 nucleotides or more, or even 200 nucleotides or more). The donor polynucleotide also contains a central region containing the mutation or other DNA sequence of interest, which is flanked by the homology arms. Thus, the overall length of the donor polynucleotide is typically greater than the total length of both homology arms (e.g., about 15 nucleotides or more, about 20 nucleotides or more, 50 nucleotides or more, 100 nucleotides or more, 150 nucleotides or more, or even 200 nucleotides or more, 250 nucleotides or more, 500 nucleotides or more, 1000 nucleotides or more, 5000 nucleotides or more).

The donor polynucleotide sequence is typically not identical to the target genomic sequence. Rather, the donor polynucleotide sequence may contain one or more single base changes, insertions, deletions, inversion or rearrangements with respect to the genomic sequence, so long as the homology arms have sufficient sequence identity to support HDR. The donor polynucleotide sequence may further comprise sequences that facilitate detection of successful insertion of the donor polynucleotide.

The ends of the donor polynucleotide may be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

In some embodiments, the donor polynucleotide (e.g., donor DNA) is covalently linked to the 5' end of the Cpf1 crRNA, the 5' end of the processing sequence, or the 5' end of the extensions sequence. In a preferred embodiment, the donor polynucleotide is linked to the 5' end of the extension sequence. In some embodiments, the linkage between the donor DNA and the nucleic acid is reversible (e.g., disulfide bond).

In some embodiments, the donor DNA is covalently linked to the nucleic acid construct. For instance, the donor polynucleotide can be linked to the processing sequence and serve as an extension sequence located 5' of the processing sequence. In another embodiment, the donor polynucleotide can be linked 5' of an extension sequence.

The nucleic acid and donor DNA can be linked or conjugated by any method known in the art. In some embodiments, the 3' end of the donor DNA and the 5' end of the nucleic acid are modified to facilitate linkage. For example, the 5' end of the nucleic acid can be activated with a thiopyridine while the donor DNA can be thiol terminated, thereby allowing a disulfide bond to form between the two molecules. In some embodiments a bridge DNA, complementary to both the nucleic acid and donor DNA, hybridizes and brings the two molecules in proximity to facilitate the reaction. FIGS. 5A-5C provide a non-limiting example of the synthesis of donor DNA conjugation to the nucleic acid.

In other embodiments, the nucleic acid and donor DNA can be conjugated via functional groups, such as functional groups that participate in bioorthogonal or "click" chemistry reactions. For example, the 5' end of the nucleic acid can be chemically modified with a functional group, such as an azide, a tetrazine, alkyne, strained alkene, or strained alkyne, and the 3' end of the donor DNA can be chemically modified with the appropriately paired functional group. For instance, if the nucleic acid contains an azide, the azide will react with an alkyne group of the donor DNA via azide-alkyne cycloaddition (copper catalyzed), or will react with a strained alkyne group of the donor DNA via azide-strained alkyne cycloaddition (no catalyst required). Likewise, if the nucleic acid contains a tetrazine, it will react with a strained alkene via tetrazine/alkene cycloaddition. Similarly, the opposite configuration can be used, e.g., if the nucleic acid contains is an alkyne, strained alkyne, or strained alkene, it will react with an azide or a tetrazine group of the donor DNA by the same cycloaddition reaction.

In some embodiments, the nucleic acid and donor DNA are conjugated via a linker. For example, the nucleic acid and donor DNA can be conjugated by a self-immolative linker. As used herein a "self-immolative linker" is a linker that hydrolyzes under specific conditions (e.g., specific pH values) allowing for release of the donor DNA from the nucleic acid.

The linker of the nucleic acid donor DNA conjugate encompasses any linker known in that art that is able to covalently link the donor DNA to the nucleic acid. The linker can be attached to the donor DNA and nucleic acid at either termini. However, in some embodiments, the linker is attached to the 5' terminus of the nucleic acid (e.g., 5' end of the crRNA, processing sequence, or extension sequence) and the 3'end of the donor DNA. The linker can be attached to the nucleic acid and donor DNA by any method known in the art, such as those described herein with respect to the conjugation of donor DNA to the nucleic acid.

In another embodiment, the donor polynucleotide can be hybridized to the extension sequence and/or processing sequence. Thus, for instance, the extension sequence can comprise a sequence that is sufficiently complementary to the donor polynucleotide to facilitate hybridization.

When a donor nucleic acid is covalently or non-covalently linked to the extension sequence, it will sometimes be desirable that the donor nucleic acid is linked to an extension sequence or portion thereof that is not cleaved by Cpf1 crRNA, such that the donor nucleic acid is closely associated with the crRNA when the target gene is edited by Cpf1. It is believed that, in some cases, improved gene editing can be attained by such a construct. Extension sequences that are not cleaved by Cpf1 include, for instance, extension sequences comprising one or more modified internucleotide linkages or synthetic nucleotides, as described above.

Compositions and Carriers

The invention also comprises a composition comprising any of the nucleic acid molecules described herein and a carrier. Any suitable carrier for nucleic acid delivery can be used. In some embodiments, the carrier can comprise a molecule capable of interacting with any of the nucleic acids described herein and facilitating the entry of the nucleic acid into a cell.

In some embodiments, the carrier comprises cationic lipids. Cationic lipids are amphiphilic molecules that have a positively charged polar head group linked via an anchor to an apolar hydrophobic domain generally comprising two alkyl chains. In some embodiments the cationic lipids form a liposome (e.g., lipid vesicle) around the nucleic acid construct and, optionally, a Cpf1 protein. Thus, in a related aspect, there is provided a liposome comprising the nucleic acid construct and, optionally, a Cpf1 protein.

In yet another embodiment the carrier comprises a cationic polymer. Examples of cationic polymers of the inventive composition include polyethylene imine (PEI), poly (arginine), poly(lysine), poly(histidine), poly-[2-{(2-aminoethyl)amino}-ethyl-aspartamide](pAsp(DET)), a block co-polymer of poly(ethylene glycol) (PEG) and poly (arginine), a block co-polymer of PEG and poly(lysine), a block co-polymer of PEG and poly{N—[N-(2-aminoethyl)-2-aminoethyl]aspartamide} (PEG-pAsp[DET], ({2,2-bis [(9Z,12Z)-Octadeca-9,12-dien-1-yl]-1,3-dioxan-5-yl}methyl) dimethylamine, (3aR,5s,6aS)—N,N-dimethyl-2,2-di((9Z,12Z)-octadeca-9,12-dien-1-yl)tetrahydro-3aH-cyclopenta[d][1,3]dioxol-5-amine, (3aR,5r,6aS)—N,N-dimethyl-2,2-di((9Z,12Z)-octadeca-9,12-dien-1-yl) tetrahydro-3aH-cyclopenta[d][1,3]dioxol-5-amine, (3aR,5R,7aS)—N,N-dimethyl-2,2-di((9Z,12Z)-octadeca-9,12-dien-1-yl)hexahydrobenzo[d][1,3]dioxol-5-amine, (3aS,5R,7aR)—N,N-dimethyl-2,2-di((9Z,12Z)-octadeca-9,12-dien-1-yl)hexahydrobenzo[d][1,3]dioxol-5-amine, (2-{2,2-bis [(9Z,12Z)-Octadeca-9,12-dien-1-yl]-1,3-dioxan-4-yl}ethyl) dimethylamine, (3aR,6aS)-5-methyl-2-((6Z,9Z)-octadeca-6,9-dien-1-yl)-2-((9Z,12Z)-octadeca-9,12-dien-1-yl) tetrahydro-3aH-[1,3]dioxolo[4,5-c]pyrrole, (3aS,7aR)-5-methyl-2,2-di((9Z,12Z)-octadeca-9,12-dien-1-yl) hexahydro-[1,3]dioxolo[4,5-c]pyridine, (3aR,8aS)-6-methyl-2,2-di((9Z,12Z)-octadeca-9,12-dien-1-yl)hexahydro-3aH-[1,3]dioxolo[4,5-d]azepine, (6Z,9Z,28Z,31Z)-heptatriaconta-6,9,28,31-tetraen-19-yl 2-(dimethylamino) acetate, (6Z,9Z,28Z,31Z)-heptatriaconta-6,9,28,31-tetraen-19-yl 3-(dimethylamino)propanoate, [6Z,9Z,28Z,31Z)-heptatriaconta-6,9,28,31-tetraen-19-yl-4-(dimethylamino) butanoate], (6Z,9Z,28Z,31Z)-heptatriaconta-6,9,28,31-tetraen-19-yl 5-(dimethylamino)pentanoate, (6Z,9Z,28Z,31Z)-heptatriaconta-6,9,28,31-tetraen-19-yl 6-(dimethylamino)hexanoate, (3-{2,2-bis[(9Z,12Z)-Octadeca-9,12-dien-1-yl]-1,3-dioxan-4-yl}propyl)dimethylamine, 1-((3aR,5r,6aS)-2,2-di((9Z,12Z)-octadeca-9,12-dien-1-yl)tetrahydro-3aHcyclopenta[d][1,3]dioxol-5-yl)-N,N-dimethylmethanamine, 1-((3aR,5s,6aS)-2,2-di((9Z,12Z)-octadeca-9,12-dien-1-yl)tetrahydro-3aHcyclopenta[d][1,3] dioxol-5-yl)-N,N-dimethylmethanamine, 8-methyl-2,2-di ((9Z,12Z)-octadeca-9,12-dien-1-yl)-1,3-dioxa-8-azaspiro [4.5]decane, 2-(2,2-di((9Z,12Z)-octadeca-9,12-dien-1-yl)-1,3-dioxolan-4-yl)-N-methyl-N-(pyridin-3-ylmethyl) ethanamine, 1,3-bis(9Z,12Z)-Octadeca-9,12-dien-1-yl 2-[2-(dimethylamino)ethyl]propanedioate, N,N-dimethyl-1-((3aR,5R,7aS)-2-((8Z,11Z)-octadeca-8,11-dien-1-yl)-2-((9Z,12Z)-octadeca-9,12-dien-1-yl)hexahydrobenzo[d][1,3] dioxol-5-yl)methanamine, N,N-dimethyl-1-((3aR,5S,7aS)-2-((8Z,11Z)-octadeca-8,11-dien-1-yl)-2-((9Z,12Z)-octadeca-9,12-dien-1-yl)hexahydrobenzo[d][1,3]dioxol-5-yl)methanamine, (1s,3R,4S)—N,N-dimethyl-3,4-bis((9Z,12Z)-octadeca-9,12-dien-1-yloxy)cyclopentan amine, (1s,3R,4S)—N,N-dimethyl-3,4-bis((9Z,12Z)-octadeca-9,12-dien-1-yloxy)cyclopentan amine, 2-(4,5-di((8Z,11Z)-heptadeca-8,11-dien-1-yl)-2-methyl-1,3-dioxolan-2-yl)-N,N-dimethylethanamine, 2,3-di((8Z,11Z)-heptadeca-8,11-dien-1-yl)-N,N-dimethyl-1,4-dioxaspiro[4.5]decan-8-amine, (6Z,9Z,28Z,31Z)-heptatriaconta-6,9,28,31-tetraen-19-yl 4-(diethylamino)butanoate, (6Z,9Z,28Z,31Z)-heptatriaconta-6,9,28,31-tetraen-19-yl 4-[bis(propan-2-yl) amino]butanoate, N-(4-N,N-dimethylamino)butanoyl-(6Z,9Z,28Z,31Z)-heptatriaconta-6,9,28,31-tetraen-19-amine, (2-{2,2-bis[(9Z,12Z)-Octadeca-9,12-dien-1-yl]-1,3-dioxan-5-yl}ethyl)dimethylamine, (4-{2,2-bis[(9Z,12Z)-Octadeca-9,12-dien-1-yl]-1,3-dioxan-5-yl}butyl)dimethylamine, (6Z,9Z,28Z,31Z)-heptatriaconta-6,9,28,31-tetraen-19-yl (2-(dimethylamino)ethyl)carbamate, 2-(dimethylamino)ethyl (6Z,9Z,28Z,31Z)-heptatriaconta-6,9,28,31-tetraen-19-ylcarbamate, (6Z,9Z,28Z,31Z)-heptatriaconta-6,9,28,31-tetraen-19-yl 3-(ethylamino)propanoate, (6Z,9Z,28Z,31Z)-heptatriaconta-6,9,28,31-tetraen-19-yl 4-(propan-2-ylamino) butanoate, N1,N1,N2-trimethyl-N2-((11Z,14Z)-2-((9Z,12Z)-octadeca-9,12-dien-1-yl)icosa-11,14-dien-1-yl) ethane-1,2-diamine, 3-(dimethylamino)-N-((11Z,14Z)-2-((9Z,12Z)-octadeca-9,12-dien-1-yl)icosa-11,14-dien-1-yl) propanamide, (6Z,9Z,28Z,31Z)-heptatriaconta-6,9,28,31-tetraen-19-yl 4-(methylamino)butanoate, Dimethyl({4-[(9Z,12Z)-octadeca-9,12-dien-1-yloxy]-3-{[(9Z,12Z)-octadeca-9,12-dien-1-yloxy]methyl}butyl})amine, 2,3-di((8Z,11Z)-heptadeca-8,11-dien-1-yl)-8-methyl-1,4-dioxa-8-azaspiro [4.5]decane, 3-(dimethylamino)propyl (6Z,9Z,28Z,31Z)-heptatriaconta-6,9,28,31-tetraen-19-ylcarbamate, 2-(dimethylamino)ethyl ((11Z,14Z)-2-((9Z,12Z)-octadeca-9,12-dien-1-yl)icosa-11,14-dien-1-yl)carbamate, 1-((3aR,4R,6aR)-6-methoxy-2,2-di((9Z,12Z)-octadeca-9,12-dien-1-yl)tetrahydrofuro[3,4-d][1,3]dioxol-4-yl)-N,N-dimethylmethanamine, (6Z,9Z,28Z,31Z)-heptatriaconta-6,9,28,31-tetraen-19-yl 4-[ethyl(methyl)amino]butanoate, (6Z,9Z,28Z,31Z)-heptatriaconta-6,9,28,31-tetraen-19-yl 4-aminobutanoate, 3-(dimethylamino)propyl ((11Z,14Z)-2-((9Z,12Z)-octadeca-9,12-dien-1-yl)icosa-11,14-dien-1-yl)

carbamate, 1-((3aR,4R,6aS)-2,2-di((9Z,12Z)-octadeca-9,12-dien-1-yl)tetrahydrofuro[3,4-d][1,3]dioxol-4-yl)-N,N-dimethylmethanamine, (3aR,5R,7aR)—N,N-dimethyl-2,2-di((9Z,12Z)-octadeca-9,12-dien-1-yl)hexahydrobenzo[d][1,3]dioxol-5-amine, (11Z,14Z)—N,N-dimethyl-2-((9Z,12Z)-octadeca-9,12-dien-1-yl)icosa-11,14-dien-1-amine, (3aS,4S,5R,7R,7aR)—N,N-dimethyl-2-((7Z,10Z)-octadeca-7,10-dien-1-yl)-2-((9Z,12Z)-octadeca-9,12-dien-1-yl)hexahydro-4,7-methanobenzo[d][1,3]dioxol-5-amine, N,N-dimethyl-3,4-bis((9Z,12Z)-octadeca-9,12-dien-1-yloxy)butan-1-amine, and 3-(4,5-di((8Z,11Z)-heptadeca-8,11-dien-1-yl)-1,3-dioxolan-2-yl)-N,N-dimethylpropan-1-amine. Any combination of the foregoing polymers also can be used.

In other embodiments, the carrier comprises a polymer nanoparticle. For instance, the inventive composition can be administered as a nanoparticle as described International Patent Application No. PCT/US2016/052690, the entire disclosure of which is expressly incorporated by reference.

Cpf1 Polypeptide or Nucleic Acid Encoding Same

In some embodiments, including the above liposomal embodiments, the composition also comprises a Cpf1 polypeptide or nucleic acid encoding same. Any Cpf1 polypeptide can be used in the inventive composition, although the Cpf1 chosen should be appropriately selected so as to work in combination with the crRNA of the nucleic acid construct in the composition to cleave a target nucleic acid and/or cleave the processing sequence of the nucleic acid construct as applicable. The Cpf1 of the composition can be a naturally occurring Cpf1 or a variant or mutant Cpf1 polypeptide. In some embodiments, the Cpf1 polypeptide is enzymatically active, e.g., the Cpf1 polypeptide, when bound to a guide RNA, cleaves a target nucleic acid. In some embodiments, the Cpf1 polypeptide exhibits reduced enzymatic activity relative to a wild-type Cpf1 polypeptide (e.g., relative to a Cpf1 polypeptide comprising the amino acid sequence depicted in FIG. 8 (SEQ ID NO: 1)), and retains DNA binding activity. Mutations that alter the enzymatic activity of Cpf1 are known in the art.

For example, Cpf1 can be from a bacterium of the genus *Acidaminococcus* or from the genus Lachnospiraceae, or from any genus or species identified in FIG. 9. An example of a Cpf1 protein sequence is provided in FIG. 8. In some embodiments, a Cpf1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the amino acid sequence depicted in FIG. 8. In some embodiments, a Cpf1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the amino acid sequence depicted in FIG. 8.

In some embodiments, a Cpf1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of a Cpf1 polypeptide of the amino acid sequence depicted in FIG. 8. In some embodiments, a Cpf1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of a Cpf1 polypeptide of the amino acid sequence depicted in FIG. 8. In some embodiments, a Cpf1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of a Cpf1 polypeptide of the amino acid sequence depicted in FIG. 8.

In some embodiments, the Cpf1 polypeptide is an FnCpf1, Lb3Cpf1, BpCpf1, PeCpf1, SsCpf1, AsCpf1, Lb2Cpf1, CMtCpf1, EeCpf1, MbCpf1, LiCpf1, LbCpf1, PcCpf1, PdCpf1, or PmCPf1; or a Cpf1 polypeptide that comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity thereto.

In some embodiments, the Cpf1 polypeptide comprises an amino acid substitution (e.g., a D→A substitution) at an amino acid residue corresponding to position 917 of the amino acid sequence depicted in FIG. 8; and/or comprises an amino acid substitution (e.g., an E→A substitution) at an amino acid residue corresponding to position 1006 of the amino acid sequence depicted in FIG. 8; and/or comprises an amino acid substitution (e.g., a D→A substitution) at an amino acid residue corresponding to position 1255 of the amino acid sequence depicted in FIG. 8.

The Cpf1 polypeptide also can be an RNase inactivated Cpf1, such as a Cpf1 comprising a modification at H800A, K809A, K860A, F864A, or R790A of *Acidaminococcus* Cpf1 (AsCpf1) or corresponding position of a different Cpf1 ortholog. Examples of mutant Cpf1 proteins include those disclosed in Zetsche et al., "Multiplex Gene Editing by CRISPR-Cpf1 Through Autonomous Processing of a Single crRNA Array," *Nat. Biotechnol.* 2017, 35 (1), 31-34. The Cpf1 polypeptide also can be a dCpf1 base editor (e.g., a Cpf1-cytosine deaminase fusion protein). Examples include, for instance, proteins disclosed in Li et al., *Nature Biotechnology,* 36 324-327 (2018) and Mahfouz et al., *Biochem J.,* 475(11), 1955-1964 (2018). An example of a synthetic variant Cpf1 is the MAD7 Cpf1 orthologue by Inscripta, Inc. (CO, USA). Additional examples of Cpf1 proteins include any of those Cpf1 proteins, including chimeric or mutant proteins, disclosed in International Patent Application No. PCT/US2016/052690, the entire disclosure of which is expressly incorporated by reference herein.

Other Nucleic Acids

The composition can further comprise other nucleic acids in addition to the crRNA. For instance, the composition can comprise a donor polynucleotide, as described herein. Alternatively, or in addition, the composition can comprise one or more additional nucleic acids that are not donor polynucleotides (e.g., a nucleic acid that has no significant sequence identity to a target sequence to be edited (e.g., a level of sequence identity that is insufficient to allow homologous recombination), or to any endogenous nucleic acid sequence of the cell to be edited. These additional nucleic acids can be RNA or DNA, such as a single stranded RNA or DNA molecule (or a hybrid molecule comprising both RNA and DNA, optionally with synthetic nucleic acid residues). The additional nucleic acid can be any length, such as at least 5 nucleotides in length (e.g., 10 nucleotides or more, 15 nucleotides or more, 20 nucleotides or more, 50 nucleotides or more, 100 nucleotides or more, 150 nucleotides or more, or even 200 nucleotides or more). In some embodiments, the nucleic acid might comprise 500 nucleotides or more, 1000 nucleotides or more, or even 5000 nucleotides or more). However, in most instances, the nucleic acid will comprise about 5000 nucleotides or less, such as about 1000 nucleotides or less, or even 500 nucleotides or less (e.g., 200 nucleotides or less).

The composition can further comprise a nucleic acid that encodes a particular protein of interest, for instance, an RNA-guided endonuclease (e.g., a Cpf1 polypeptide). The RNA-guided endonuclease can be any as described herein with respect to other aspects of the invention.

Divalent Metal Ions

In some embodiments the composition is substantially or completely free of a divalent metal ion (e.g., magnesium) that activates the particular Cpf1 protein used so as to reduce or prevent premature cleavage of the processing sequence prior to delivery. The composition is considered substantially free of magnesium what the concentration does not allow for Cpf1 self-processing enzymatic activity. In some embodiments the composition comprises about 20 mM or less NaCl and is substantially or completely free of magnesium or other divalent ions that activates the Cpf1 protein.

Method of Genetically Modifying a Eukaryotic Cell

The invention also provides a method of genetically modifying a eukaryotic target cell, comprising contacting the eukaryotic target cell with any of the nucleic acids or compositions described herein (e.g., a nucleic acid comprising a Cpf1 crRNA, an extension sequence 5' of the crRNA, and, optionally, a processing sequence between the crRNA and the extension sequence) to genetically modify a target nucleic acid. In some embodiments, the Cpf1 crRNA of the nucleic acid comprises a targeting sequence (e.g., 3' of the stem-loop domains) that hybridizes with a target sequence in the target cell. In some embodiments, the Cpf1 crRNA comprises a processing sequence, which is cleaved upon entry into the cell, thereby releasing the Cpf1 crRNA from the processing sequence and the extension sequence. In other embodiments, the Cpf1 crRNA does not comprise a processing sequence.

Target nucleic acid is a polynucleotide (e.g., RNA, DNA) to which the targeting sequence of the crRNA will bind and induce cleavage by Cpf1. A target nucleic acid comprises a "target site" or "target sequence" which is a sequence present in a target nucleic to which the crRNA hybridizes which, in turn, guides the endonuclease to the target nucleic acid.

A "eukaryotic target cell" may be any eukaryotic cell known in the art and comprises both cells in vivo and in vitro. In an embodiment, the target cell is a mammalian cell.

Any route of administration can be used to deliver the composition to the mammal. Indeed, although more than one route can be used to administer the composition, a particular route can provide a more immediate and more effective reaction than another route. When administered to cells in vitro or ex vivo, the nucleic acid or composition can be contacted to the cell by any suitable method. For instance, the nucleic acid can be in a liposome, encapsulated by a cationic polymer, and/or introduced by electroporation. When administered to a subject, such as a mammal or human, the composition can be administered by any of a variety of routes. For instance, a dose of composition also can be applied or instilled into body cavities, absorbed through the skin (e.g., via a transdermal patch), inhaled, ingested, topically applied to tissue, or administered parenterally via, for instance, intravenous, intraperitoneal, intraoral, intradermal, subcutaneous, or intra-arterial administration.

The composition can be administered in or on a device that allows controlled or sustained release, such as a sponge, biocompatible meshwork, mechanical reservoir, or mechanical implant. Implants (see, e.g., U.S. Pat. No. 5,443,505), devices (see, e.g., U.S. Pat. No. 4,863,457), such as an implantable device, e.g., a mechanical reservoir or an implant or a device comprised of a polymeric composition, are particularly useful for administration of the composition. The composition also can be administered in the form of sustained-release formulations (see, e.g., U.S. Pat. No. 5,378,475) comprising, for example, gel foam, hyaluronic acid, gelatin, chondroitin sulfate, a polyphosphoester, such as bis-2-hydroxyethyl-terephthalate (BHET), and/or a polylactic-glycolic acid.

EXAMPLES

The following examples further illustrate the invention but, of course, should not be construed as in any way limiting its scope. Table 2, below, provides the sequences of nucleic acids used in these experiments.

TABLE 2

| Supplementary Table 1 | |
|---|---|
| sgRNAfor Cas9 | rGrCrCrGrUrCrCrArGrCrUrCrGrArCrCrArGrGrArGrUrUrUrUrArGrArGrC rUrArGrArArArUrArGrCrArArGrUrUrArArArArUrArArGrGrCrUrArGrUrC rCrGrUrUrArUrCrArArCrUrUrGrArArArArArGrUrGrGrCrArCrCrGrArGrU rCrGrGrUrGrCrUrUrUrU |
| crRNA$^{+4}$ | rUrGrGrArUrArArUrUrUrCrUrArCrUrCrUrUrGrUrArGrArUrCrGrUrCrGrC rCrGrUrCrCrArGrCrUrCrGrArCrCrA |
| crRNA$^{+9}$ | rGrGrGrArArUrGrGrArUrArArUrUrUrCrUrArCrUrCrUrUrGrUrArGrArUrC rGrUrCrGrCrCrGrUrCrCrArGrCrUrCrGrArCrCrA |
| crRNA$^{+9}$ scrambled | rGrGrUrGrArGrCrArArUrArArUrUrUrCrUrCrUrUrGrUrArGrArUrCrGrUrC rGrCrCrGrUrCrCrArGrCrUrCrGrArCrCrA |
| crRNA$^{+9}$dU | rGrGrUrGrArGrCrAUrUrArArUrUrUrCrUrArCrUrCrUrUrGrUrArGrArUrCr GrUrCrGrCrCrGrUrCrCrArGrCrUrCrGCrArCrCrA |
| crRNA$^{+9}$S | rA*rU*rG*rG*rU*rG*rA*rG*C*rUrArArUrUrUrCrUrArCrUrCrUrUrGrUrA rGrArUrCrGrUrCrGrCrCrGrUrCrCrArGrCrUrCrGrArCrCrA |

TABLE 2-continued

| Supplementary Table 1 | |
|---|---|
| crRNA$^{+15}$ | rGrU rCrArA rArGrG rGrArA rUrGrG rArUrA rArUrU rUrCrU rArCrU<br>rCrUrU rGrUrA rGrArU rCrGrU rCrGrC rCrGrU rCrCrA rGrCrU<br>rCrGrA rCrCrA |
| crRNA$^{+25}$ | rArUrG rUrGrU rUrUrU rUrGrU rCrArA rArArG rArCrC rUrUrU<br>rUrUrA rArUrU rUrCrU rArCrU rCrUrU rGrUrA rGrArU rCrGrU<br>rCrGrC rCrGrU rCrCrA rGrCrU rCrGrA rCrCrA |
| crRNA$^{+59}$ | rGrGrCrCrArGrCrUrUrGrCrCrGrGrUrUrUrUrUrArGrUrCrGrUrGrCrUrG<br>rCrUrUrCrArUrGrUrGrUrUrUrUrGrUrCrArArArArGrArCrCrUrUrUrUrU<br>rArArUrUrUrCrUrArCrUrCrUrUrGrUrArGrArUrCrGrUrCrGrCrCrGrUrCrC<br>rArGrCrUrCrGrArCrCrA |
| crRNA$^{+59}$_D2 | rUrCrArArArArGrArCrCrUrUrUrUrGrUrCrArArArArGrArCrCrUrUrUrUrG<br>rUrCrArArArArGrArCrCrUrUrUrUrGrUrCrArArArArGrArCrCrUrUrUrUrU<br>rArArUrUrUrCrUrArCrUrCrUrUrGrUrArGrArUrCrGrUrCrGrCrCrGrUrCrC<br>rArGrCrUrCrGrArCrCrA |
| crRNA$^{+59}$_D3 | rGrGrCrGrGrCrUrUrGrCrCrGrGrUrUrUrUrUrArGrUrCrGrUrGrCrUrGrC<br>rUrUrCrArUrGrUrGrUrUrUrUrUrGrUrCrUrArArGrArArCrUrUrUrArArArU<br>rArArUrUrUrCrUrArCrUrCrUrUrGrUrArGrArUrCrGrUrCrGrCrCrGrUrCrC<br>rArGrCrUrCrGrArCrCrA |
| Ai9 crRNA | rUrArArUrUrUrCrUrArCrUrCrUrUrGrUrArGrArUrUrCrCrArArArCrUrCrA<br>rUrCrArArUrGrUrArUrCrU |
| Ai9 crRNA$^{+2}$ | rUrUrUrArArUrUrUrCrUrArCrUrCrUrUrGrUrArGrArUrUrCrCrArArArCrU<br>rCrArUrCrArArUrGrUrArUrCrU |
| Ai9 crRNA$^{+9}$ | rArGrArCrCrUrUrUrUrUrArArUrUrUrCrUrArCrUrCrUrUrGrUrArGrArUrU<br>rCrCrArArArCrUrCrArUrCrArArUrGrUrArUrCrU |
| Ai9 crRNA$^{+59}$ | rGrArGrCrArGrCrUrUrGrCrCrGrGrUrUrUrUrUrArGrUrCrGrUrGrCrUrG<br>rCrUrUrCrArUrGrUrGrUrUrUrUrUrGrUrCrArArArArGrArCrCrUrUrUrUrU<br>rArArUrUrUrCrUrArCrUrCrUrUrGrUrArGrArUrUrCrCrArArArCrUrCrArU<br>rCrArArUrGrUrArUrCrU |
| Serpina1 crRNA | rUrArArUrUrUrCrUrArCrUrCrUrUrGrUrArGrArUrUrCrGrUrCrGrArUrGrG<br>rUrCrArGrCrArCrArGrCrC |
| Serpina1 crRNA$^{+9}$ | rCrUrCrCrCrCrUrCrCrUrArArUrUrUrCrUrArCrUrCrUrUrGrUrArGrArUrU<br>rCrGrUrCrGrArUrGrGrUrCrArGrCrArCrArGrCrC |
| ssODN with Clal restriction enzyme site | CTCGCCGGACACGCTGAACTTGTGGCCGCTTACGTCGCCGTCCAGCTCGACCATCGATGG<br>GCACCACCCCGGTGAACAGCTCCTCGCCCTTGCTCACCAT |
| ssDNA without any homology | GGGATAGACATGGGTATGGCCTCTAAAAACATGGCGCCAGCAGCTTCAGTCCCTTTCTCA<br>TCGATGGTCAGCACAGCCTTATGCACGGCCTGGAGGGGAG |
| ssDNA for ai9 myoblast experiment | CTTGACCTCGGGGGGGATAGACATGGGTATGGCCTCTAAAAACATGGCgCCAGCAGCTTC<br>AGTCCCTTTCTCATCGATGGTCAGCACAGCCTTATGCACG |
| ssRNA for ai9 myoblast experiment | rArGrArArArGrGrGrArCrUrGrArArGrCrUrGrCrUrGrUrU rUrUrA rGrArG<br>rCrUrA rGrArA rArUrA rGrCrA rArGrU rUrArA rArArU rArArG<br>rGrCrU rArGrU rCrCrG rUrUrA rUrCrA rArCrU rUrGrA rArArA<br>rArGrU rGrGrC rArCrC rGrArG rUrCrG rGrUrG rCrUrU rUrU |
| 9nt ssRNAfor GFP-HEK experiment | rGrGrGrArArUrGrGrA |
| 100nt ssRNAfor GFP-HEK experiment | rArArGrUrArArArArCrCrUrCrUrArCrArArArUrGrGrUrUrUrUrArGrArGrC<br>rUrArGrArArArUrArGrCrArArGrUrUrArArArArUrArArGrGrCrUrArGrUrC<br>rCrGrUrUrArUrCrArArCrUrUrGrArArArArArGrUrGrGrCrArCrCrGrArGrU<br>rCrGrGrUrGrCrUrUrUrU |

*phosphorothioate

U: 2' Deoxy

Underline: pre-crRNA sequences

Example 1

This example illustrates that unmodified Cpf1 crRNA tends to provide lower gene editing efficiency as compared to Cas9 sgRNA.

SpCas9 and AsCpf1, both without extension of the guide RNA, were compared using a green fluorescent protein (GFP) reporter system. A matched protospacer DNA sequence in the GFP gene that could be recognized by both nucleases was selected in order to directly compare AsCpf1 and SpCas9. The systems are illustrated in FIG. 13A. The RNP complexes were introduced into HEK293T cells expressing the GFP gene under the control of a doxycycline-inducible promoter (GFP-HEK) using both electroporation and cationic lipids. Editing activity was determined by measuring the population of GFP negative cells, with GFP being disrupted through NHEJ-mediated indel mutations.

AsCpf1 RNP exhibited lower gene editing than SpCas9 in both the electroporated and Lipofectamine treated cells (FIGS. 13B and 13C). AsCpf1 RNP electroporated cells were 31% GFP negative, while SpCas9 RNP electroporated cells were 41% GFP negative (FIG. 13B). With the Lipofectamine and RNAiMax delivery systems, AsCpf1 treated cells were approximately 8% GFP negative while SpCas9 treated cells were approximately 30% GFP negative (FIG. 13C).

Example 2

This example demonstrates that a nucleic acid comprising Cpf1 crRNA, a processing sequence 5' of the Cpf1 crRNA, and an extension sequence 5' of the processing sequence (reversibly supercharged crRNA) enhances delivery of Cpf1 by cationic lipids in vitro.

Cationic materials such as lipofectamine and polycations are the most commonly used delivery vehicles for nucleic acids in cells and living animals. Therefore, efficiency of the cationic lipid lipofectamine to transfect Cpf1/crRNA complexes into green fluorescent protein expressing HEK cells (GFP-HEK) was analyzed. Briefly, crRNA designed to knock down the GFP gene via indel formation was complexed with Cpf1 and either electroporated (nucleofection) into cells or transfected with lipofectamine. The gene editing efficiency was then determined by measuring the number of GFP knockout cells, via flow cytometry, wherein cells that no longer express GFP indicate that the cell was transfected with the Cpf1/crRNA complex.

Figure 1A:
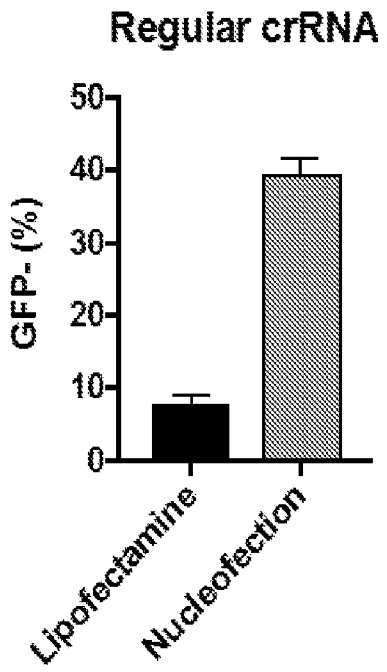
FIG. 1A is a graph comparing delivery of unmodified crRNA in complex with Cpf1 using either lipofectamine or electroporation (nucleofection).

The results from these experiment show that lipofectamine cannot efficiently transfect unmodified Cpf1 crRNA complexes (FIG. 1A). Specifically, cells treated with lipofectamine and Cpf1/crRNA complexes had only an 8% NHEJ efficiency, whereas, cells electroporated with Cpf1/crRNA complexes had a 40% NHEJ efficiency, demonstrating that delivery limitations were the major cause for the low NHEJ efficiency with lipofectamine.

To examine the effect of sequence extension, a crRNA, which is 41 nucleotides in length, was extended by 9 nucleotides (crRNA$^{+}$9) or extended by 59 nucleotides (crRNA$^{+59}$) The extension included a self-processing sequence that would self-cleave into an active crRNA. The unmodified crRNA, the crRNA$^{+}$9, and the crRNA$^{+59}$ were each individually complexed with Cpf1 and transfected into the GFP-HEK cells using lipofectamine. The RNPs were formed in low salt conditions to prevent potential processing of the 5'-end extensions. The level of NHEJ, which is an indicator of transfection efficiency, was determined by measuring the percent of GFP negative cells.

Figure 1B:
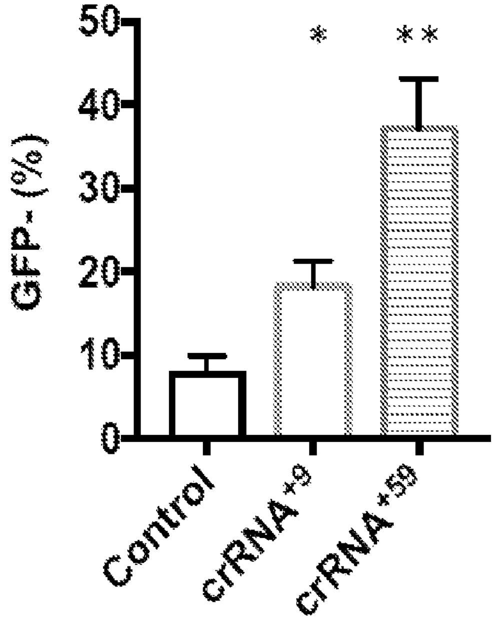
FIGS. 1B and 1C are graphs comparing the lipofectamine mediated delivery and NHEJ generation of Cpf1-crRNA complexes comprising unmodified crRNA (41 nucleotides long) and extended crRNA.
Figure 1C:
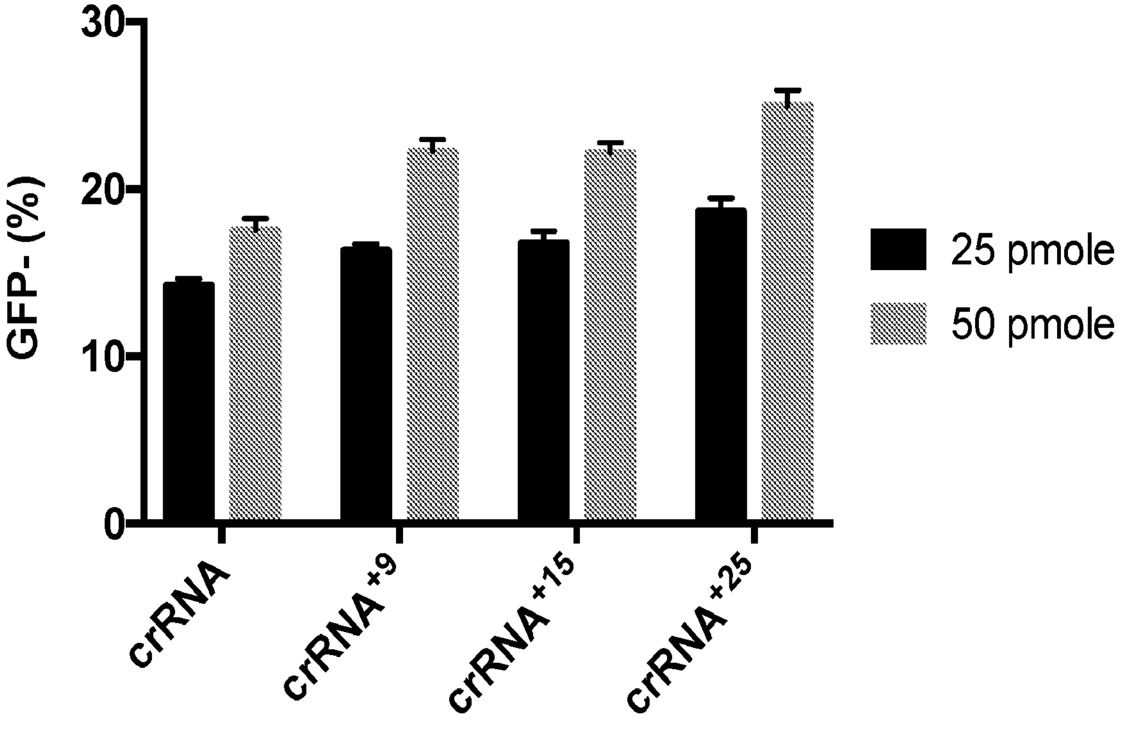

As shown in FIG. 1B, extension of crRNA with a self-processing sequence significantly enhances transfection efficiency with cationic vehicles. Cells treated with unextended crRNA via lipofectamine showed 8% GFP negative, whereas the 9-base extended crRNA treated cells were 18% GFP−, and the 59-base extended crRNA treated cells were 37%, which was approximately a 4-fold increase over the control unmodified crRNA. In addition, crRNA+9, crRNA+15, and crRNA+25 were tested with lipofectamine and showed length dependent increase of gene editing efficiency (FIG. 1C)

Figure 1D:
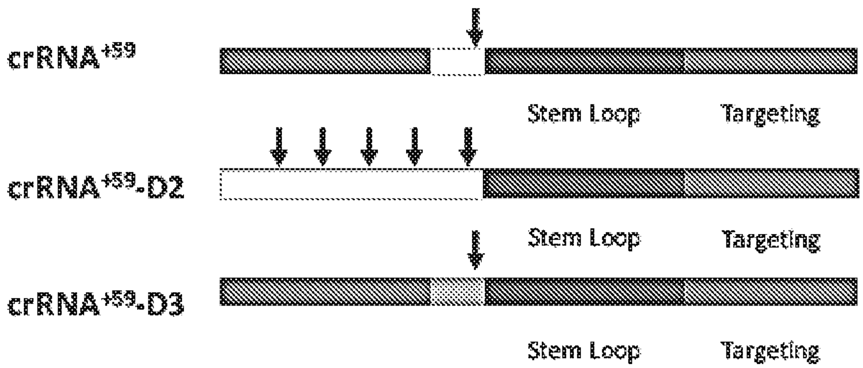
FIG. 1D is a schematic illustration of the structures of 41-nucleotide (nt) unmodified crRNA and extended crRNAs. The arrows represent Cpf1 cleavage sites.
Figure 1E:
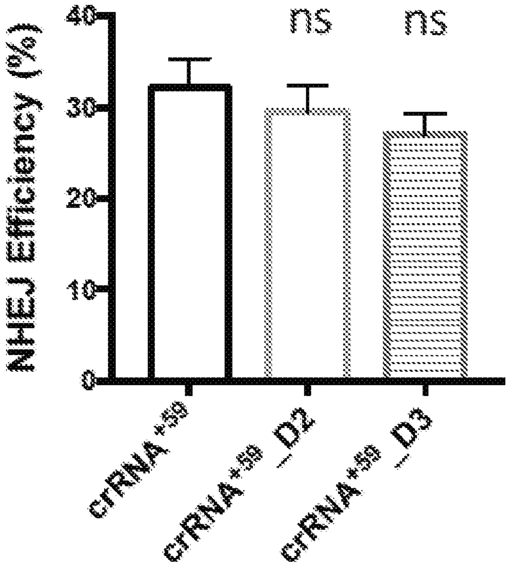
FIG. 1E is a graph showing NHEJ efficiency for the crRNA constructs illustrated in FIG. 1D.

To ascertain if there is a specific 5'-extension sequence requirement for this enhancement, three different 59 nucleotide 5' extensions were compared. The first and original 59 nucleotide extended crRNA is described above and contains one AsCpf1 pre-crRNA (crRNA+59), the second 59 base extended cRNA contains four AsCpf1 pre-crRNA sites in tandem (crRNA+59-D2), and the third 59 base extended crRNA contains the FnCpf1 pre-crRNA preceded by a scrambled DNA sequence with no homology to any sequence in the human genome (crRNA+59-D3) (FIG. 1D). These crRNAs were delivered using Lipofectamine 2000 similar to the above paragraph. All three 5' extensions showed equivalent editing activity: crRNA+59 cells were 32% GFP negative, crRNA+59_D2 cells were 30% GFP negative, and crRNA+59_D3 cells were 27% GFP negative (FIG. 1E). This suggests that there is not a stringent sequence requirement for the 5'-extension enhancement, similar to previous findings with the 9 nucleotides extended crRNAs with electroporated cells. Additionally, these results provide evidence supporting the above hypothesis that increasing the negative charge density on the crRNA, and thereby also the AsCpf1 RNP complex, can enhance the delivery of AsCpf1 to cells by cationic lipids.

The extended crRNAs were tested in an in vitro DNA cleavage assay to determine whether the extended crRNAs enhanced the inherent nuclease activity of Cpf1. No difference in activity was observed between the three crRNAs tested: wild type crRNA, crRNA$^{+9}$, and crRNA$^{+59}$ with 15 minutes and 60 minutes incubation time. crRNA$^{+59}$ even had slower DNA cleavage than wild type crRNA when the incubation time was only 5 minutes.

5' extended crRNAs were also studied to determine if there was enhanced gene editing activity in the Cpf1 if delivered by plasmid rather than as an RNP. Cpf1 plasmid was transfected 24 hours prior to electroporation of the crRNAs and the gene editing activity was determined. No improvement in gene editing efficiency was observed when the Cpf1 was produced from plasmids.

Figure 1F:
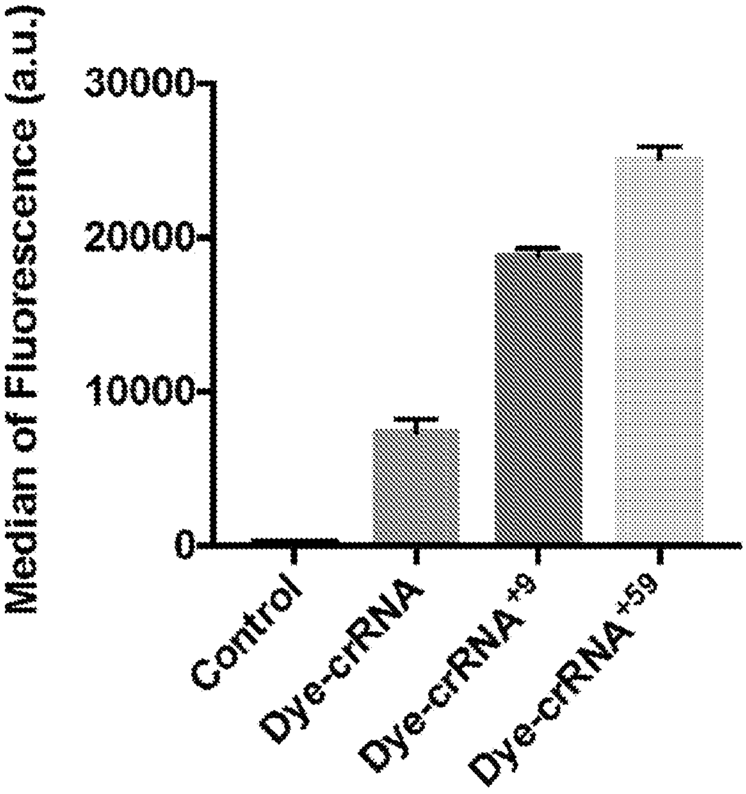
FIG. 1F is a graph depicting the cellular delivery of Cpf1 RNP using lipofectamine and crRNAs with different length labeled with fluorescent dye.

Further, the crRNAs were labeled with a fluorescence dye to determine if the extended crRNAs had enhanced uptake in cells after delivery via either electroporation or lipofectamine. Electroporation of the Cpf1 RNPs resulted in above 90% of the cells being positive for the dye-crRNA and showed highly efficient delivery regardless of the crRNA length. The delivery efficiency of Cpf1 RNP with lipofectamine was dependent on the length of the crRNA, and extended crRNAs were delivered into HEK 293T cells more efficiently than wild type crRNA (FIG. 1F).

The results show that extended crRNA as provided herein enhance delivery and gene editing efficiency.

Example 3

This example demonstrates that the activity of Cpf1 is enhanced with 5'-terminal extensions in HEK cells with electroporation.

GFP-targeting crRNAs with 5'-end extensions of 4, 9, 15, 25, and 59 nucleotides were introduced into GFP-HEK cells by electroporation as an RNP complex with AsCpf1. The sequences for the 4 to 25 nucleotide extensions were scrambled, and the 59 nucleotide extension consisted of the AsCpf1 pre-crRNA preceded by a scrambled RNA sequence with no homology to human genome sequence.

The crRNAs with the 4 to 25 nucleotide 5'-extensions all exhibited dramatically increased gene editing over the crRNA with no extension. Cells electroporated with the unextended cRNA were 30% GFP negative (crRNA), with 4 to 25 nucleotide extended crRNA were 55 to 60% GFP negative, and with 59 nucleotide extended crRNA were 37% GFP negative (FIG. 2). The gene editing levels for the 4 and 25 nucleotide 5'-extended crRNAs are comparable to that of the SpCas9 RNP electorporated cells.

The results confirm that 5' extensions of Cpf1 crRNA increase gene editing efficiency.

Example 4

This example demonstrates that a nucleic acid comprising Cpf1 crRNA and an extension sequence 5' enhances delivery of Cpf1 by cationic lipids in vivo as well as Cpf1 activity in cells.

Three different chemical modifications were investigated on crRNAs with extension: 2' O-methyl modification, phosphororthioate linkages, and deoxynucleotide ribose groups (FIG. 15A). The first 3 of the 4 nucleotides were extended with 2'-O-methyl nucleotides and 3' phosphorothioate linkage (MS), a deoxynucleotide at the $9^{th}$ position of the 9 nucleotide 5'-extended crRNA (9dU), 3' phosphorothioate linkage to all 9 nucleotides plus a deoxynucleotide at the $9^{th}$ position of the 9 nucleotide 5'-extended crRNA (9s).

Cpf1 RNP with crRNAs that had extension and chemical modifications were electroporated into GFP-HEK cells and the gene editing activity was determined by flow cytometry. Extended crRNA with chemical modifications had similar activity to unmodified extended crRNA (41% to 46% GFP negative cells) (FIG. 15D).

Also, these crRNAs were examined using a blue fluorescent protein (BFP) expressing HEK293T cell line (BFP-HEK). The results are presented in FIG. 12.

The results from this experiment show that the 5'-extensions increased the gene editing efficiency of AsCpf1 and the tolerance of the 5'-end of the crRNA for chemical modifications. Further, 5' chemical modifications of the crRNA are possible without damaging the activity, if the 5' end of the crRNA is extended.

A key benefit of using chemically modified crRNAs is that they are more stable to hydrolysis by serum nucleases. Therefore, the serum stability of the 5' chemically modified crRNA was investigated.

5' chemically modified crRNAs were incubated in diluted fetal bovine serum and their degradation was analyzed via gel electrophoresis. FIG. 15B provides a quantification of crRNA remaining after 15 minutes incubation in serum. The results show that the unmodified crRNAs rapidly degrade in serum, whereas crRNA+9s, which contains a phosphorothioate backbone, is significantly more stable to hydrolysis in serum.

5' modified crRNAs were also studied to determine if they could enhance the ability of lipofectamine to transfect Cpf1 RNP, due to its ability to protect the crRNA from nucleases in cells and in serum. Cpf1 with crRNA+$^{9}$s was more efficient at editing genes in cells than crRNA$^{+9}$ by 40%, suggesting that 5' crRNA chemical modifications, enabled by 5' crRNA extension, will have numerous applications in gene editing (FIG. 15C).

The crystal structure of Cpf1 RNP has recently been solved and demonstrates that the AsCpf1 protein forms numerous interactions with the phosphodiester backbone of the crRNA. 5'-chemical modifications of the unextended crRNA therefore has a high chance of disrupting important interactions between the crRNA and the Cpf1, resulting in a disruption of AsCpf1 gene editing activity.

In contrast, crRNA with 5' extensions appear to tolerate chemical modifications because the nucleotides interacting with the AsCpf1 protein are not modified. These results provide a methodology for introducing chemical modifications at the 5'-end of the crRNA, which can potentially enhance delivery for ex vivo and in vivo therapeutic applications. Such a construct also enables other molecules, such as a targeting ligand, endosomal escape moiety, or other functional molecules, to be conjugated to the extended crRNA and retained with the Cpf1 molecule. For instance, biotin or avidin (or streptavidin) could be conjugated to the crRNA extension, allowing the modified crRNA to bind to another molecule (e.g., targeting molecule) conjugated with streptavidin or biotin as appropriate (e.g. FIG. 14). In addition, the crRNA could be conjugated to a Cpf1 mRNA by way of the extension, allowing Cpf1 to be delivered by translation of the mRNA. Once the Cpf1 mRNA is translated and produces Cpf1 protein in the cytoplasm, Cpf1 protein will recognize the crRNA part of the construct and, optionally, process the connecting RNA sequence, separating Cpf1 mRNA and crRNA.

Example 5

Experiments were also performed to determine if crRNA with an extension sequence could enhance the ability of cationic polymers to transfect Cpf1. In particular, the various length crRNAs as used in Example 2 (crRNA with no extension, 9 nt extension, and 59 nt extension) were complexed with Cpf1, mixed with the cationic polymer PAsp (DET), and added to GFP-HEK cells. The NHEJ efficiency of the formulations was determined by measuring the frequency of GFP negative cells via flow cytometry.

As shown in FIG. 16, the 59 base 5'-extension enhanced PAsp(DET) mediated delivery of AsCpf1 RNP to the cells by 2-fold. The unextended crRNA (crRNA) was 8% GFP negative, the 9 nucleotides extended crRNA (crRNA+9) was 10% GFP negative, and the 59 nucleotides extended crRNA (crRNA+59) was 18% GFP negative. These results demonstrate that the extension sequences can improve delivery of crRNA to cells using cationic polymers.

Example 6

This example demonstrates extended crRNA enhances delivery of Cpf1 in vivo.

Experiments were performed to determine if extended crRNA (crRNA$^{+59}$) could enhance the cationic lipid mediated delivery of Cpf1 in vivo. A schematic of the experiment is provided in FIG. 3A.

The studies were performed in Ai9 mice using the previously validated spacers. Ai9 mice were given one intramuscular injection of Lipofectamine or PAsp(DET) combined with either: AsCpf1-crRNA complex or AsCpf1-crRNA$^{+59}$ complex. Two weeks after the injection, the expression of tdTomato (red fluorescence) was imaged in 10 μm sections of the gastrocnemius muscle (muscle figure in FIG. 3B). A comparison of the images collected for the unextended and extended crRNAs showed that the extended crRNA dramatically enhanced the ability of the PAsp(DET) to deliver AsCpf1 RNP in vivo. Additionally, the RNP with the extended crRNA (Cpf1 RNP+59) complexed to PAsp(DET) induced the expression of tdTomato millimeters away from the injection site as well as the entire gastrocnemius muscle. The high range of tdTomato expression in the muscle is likely due to the unique polynuclear nature of the muscle fibers. This would allow the TdTomato to be expressed over the entire length of the muscle fiber and, thus, observable over several millimeters in length.

The ability of the 59 nucleotides extended crRNA to enhance the delivery and, by extension, the editing efficiency of AsCpf1 RNP in vivo, bolsters Cpf1's value as a tool for animal research and as a potential therapeutic for treating human disease, especially genetic muscular dystrophies.

Example 7

5.1: Extended crRNA Increases HDR and NHEJ Rates

To examine whether the 5'-extension could increase HDR rates in addition to NHEJ levels, the AsCpf1 RNPs with crRNA containing various extensions were introduced into GFP-HEK cells together with a single-stranded oligonucleotide donor (ssODN). NHEJ levels were determined by measuring the population of GFP negative cells (similar to the first section), while HDR rates were quantified using a restriction enzyme digestion assay. A 2-fold improvement in HDR was observed for both the 4 and 9 nucleotides extended crRNAs (17% HDR frequency for crRNA+4 and 18% HDR frequency for crRNA+9 versus 9% for unmodified crRNA in FIG. 4A). Smaller increases in HDR were observed for the 59 base extension (13% HDR rate for crRNA+59 in FIG. 4A).

Interestingly, the ssODN used for HDR also dramatically increased the NHEJ efficiency of AsCpf1. The ssODN increased the percentage of GFP negative cells from: 30% to 46% for the unextended crRNA (crRNA), 55% to 95% for the 4 base extended crRNA (crRNA+4), 58% to 93% for the 9 base extended crRNA (crRNA+9), and 37% to 58% for the 59 base extended crRNA (crRNA+59) (FIG. 4B). The finding that exogenously added DNA enhances AsCpf1 RNP-mediated editing was further validated in the BFP reporter system. Single-stranded DNA (ssDNA) without any homology to the human genome was electroporated into BFP-HEK cells with AsCpf1 RNP. Similarly, the addition of ssDNA increased the AsCpf1 editing activity by 2-fold for both the unextended and extended crRNAs. The BFP negative population increased from: 31% to 50% for the unextended crRNA (crRNA), 59% to 91% for the 4 nucleotides extended crRNA (crRNA+4), and 60% to 95% for the 9 nucleotides extended crRNA (crRNA+9) (FIG. 4C). Additional experiments were performed to determine if the exogenously added DNA had to have homology to the Cpf1 RNP target site in order to enhance gene editing. AsCpf1 RNP was electroporated into cells along single-stranded DNA (ssDNA) without any homology to the target sequence, and the gene editing efficiency was measured. Similarly, the addition of ssDNA without homology also increased the AsCpf1 editing activity to approximately 90% for both extended crRNAs (FIG. 4D). The results demonstrate that ssDNA can augment editing with AsCpf1. Additionally, the activity enhancement with 5'-end extension was synergistic with exogenous ssDNA and collectively the gene editing they induced was close to a 100%. It was observed that the addition of ssDNA did not enhance Cpf1 gene editing efficiency if lipofectamine is used as the delivery method instead of electroporation.

It is sometimes preferably to use RNA rather than DNA for gene editing as ssRNA cannot integrate into the genome, and can be safer to use. To test for the effect of ssRNA rather than DNA, GFP-HEK cells were electroporated with Cpf1 RNP and two different ssRNAs (9nt and 100nt) and the resulting levels of gene editing were determined. Two 100nt ssRNAs with slight sequence variation both dramatically increased the gene editing efficiency of Cpf1, resulting in a 2-fold improvement, whereas the 9nt ssRNA induced a 10% enhancement in gene editing efficiency (FIG. 4E).

These results demonstrate that single stranded nucleic acids can be used to augment the Cpf1 editing activity in cells.

5.2: Single-Molecule Extended crRNA and Donor DNA.

Part 2 of this example demonstrates that extended crRNA combined with donor DNA in a single molecule can enhance HDR.

The vast majority of genetic diseases require gene correction instead of knockout, and there is therefore of great interest in developing Cpf1 based therapeutics that can correct gene mutations via HDR. To address the problem of generating nanoparticles that efficiently encapsulate both donor DNA and Cpf1-crRNA, experiments were performed to determine whether crRNA and donor DNA could be combined into a single molecule, via a reversible disulfide bond. One challenge is that 5' terminal of crRNA is quite sensitive to chemical modifications, as reported previously. Therefore, chemical modifications at the 5' end of the crRNA extended self-processing sequence were tested.

crRNA was extended with four additional nucleotides at its 5' terminal and a chemical modification (i.e., 5'DBCO, 5'thiol, or 5'azide) was added to the end of the nucleotides. The activity of 4 nt extended crRNAs was tested with and without the chemical modifications at 5' terminus. Briefly, the 5' modified supercharged crRNA, designed to knock down the GFP gene via indel formation, was complexed with Cpf1 and electroporated (nucleofection) into cells. The gene editing efficiency was then determined by measuring the number of GFP knockout cells, via flow cytometry, wherein the cells no longer expressing GFP indicate that the cell was transfected with the Cpf1/crRNA complex.

FIG. 4F shows that none of the chemical modifications or nucleotide extensions affected the Cpf1-crRNA activity, as all crRNA complexes showed about 40% GFP knockout, which is similar levels to unmodified control crRNA.

As chemistry on 5' terminal of crRNA can be added without losing activity, the 5' end of crRNA was activated with thiopyridine to react with a thiol terminated donor DNA (see FIGS. 5A-5C). Reaction between the two macromolecules have slow kinetics. Therefore, a method of using a bridge DNA that is complementary to both the crRNA and the donor DNA was used. The bridge hybridizes and brings two macromolecules in proximity to facilitate the reaction in order to enhance the conjugation yield between crRNA and donor DNA. The conjugation yield was up to 40% and the product was purified via gel extraction. The conjugate was named "Homologous DNA-crRNA" (HD-RNA). HD-RNA contains a disulfide bond, which should be reduced in the cytoplasm. Thiol mediated cleavage of HD-RNA was determined by incubating it in DTT for 6 hours, and analyzing its molecular weight via gel electrophoresis. A comparison of the gels in FIG. 5C shows that DTT reduces HD-RNA and regenerates Donor DNA and crRNA.

HD-RNA complexed with Cpf1 was electroporated into GFP-HEK cells and the levels of HDR and NHEJ were compared to cells electroporated with Cpf1-crRNA and donor DNA separately. Similar levels of NHEJ and HDR were observed from cells electroporated with HD-RNA compared to the cells electroporated with Cpf1-crRNA and donor DNA, demonstrating that conjugation of crRNA with donor DNA via disulfide bond does not affect the functionality of either the crRNA or the donor DNA.

Experiments were performed to determine whether HD-RNA enhances the HDR efficiency of Cpf1 after transfection with cationic lipids (i.e., lipofectamine) or cationic polymers (i.e., PAsp(DET)). For these experiments, HD-RNA complexed with Cpf1 was transfected into GFP-HEK cells using lipofectamine or PAsp(DET) and the levels of HDR and NHEJ were compared. NHEJ was determined by measuring the frequency of GFP negative cells, and was confirmed by performing a Surveyor assay with a PCR amplicon of the targeted region of the BFP gene. HDR efficiency was determined by isolating cellular DNA and analyzing for the presence of a restriction enzyme site embedded in the donor DNA. Results are presented in FIGS. 6 and 7.

FIGS. 6 and 7 demonstrate that HD-RNA enhanced both the NHEJ and HDR efficiency of Cpf1 after delivery with PAsp(DET). Specifically, HDR was detected in up to 60% of the cells treated with HD-RNA/Cpf1 complexed delivered with PAsp(DET), which is significantly higher than the HDR rate of cells treated with Cpf1/crRNA and donor DNA complexed with PAsp(DET). In addition, the 60% HDR rate observed with HD-RNA/Cpf1 complexed delivered with PAsp(DET) is even higher than the HDR rate observed with electroporation of Cpf1/crRNA complexes, and suggests that having Donor DNA in the vicinity of a Cpf1 cleavage site may assist with HDR.

These results demonstrate that extended crRNA can enhance HDR.

Example 9

This example demonstrates the use of extended crRNA in a different cell type, and the utility of the method to treat genetic disorders.

HD-RNA has numerous potential applications because of its capacity to enhance the ability of Cpf1 to generate HDR in cells after delivery with cationic lipids. Duchenne muscular dystrophy (DMD) was tested as an initial medical application for HD-RNA. DMD is an early onset lethal disease, caused by mutations in the dystrophin gene; it is the most common congenital myopathy, and approximately 30% of DMD patients have single base mutations or small deletions that could be potentially treated with HDR based therapeutics.

Therefore, HD-RNA, designed to target the dystrophin gene, was tested for its ability to correct the dystrophin mutation in myoblasts obtained from mdx mice via HDR. An HD-RNA was designed that could cleave the dystrophin gene and which also contained a donor DNA designed to correct the C to T mutation present in their dystrophin gene (see FIGS. 10A and 10B). The HDR rate in mdx myoblasts treated with Cpf1/HD-RNA+lipofectamine was determined and compared against mdx myoblasts treated with Cpf1-crRNA, donor DNA and lipofectamine. It was found that Cpf1 complexed to HD-RNA is more efficient at generating HDR in mdx myoblasts than cells treated with Cpf1 RNP and donor DNA. For example, HD-RNA treated cells had a 5-10% HDR rate whereas control cells, had only a 1% HDR rate.

In another experiment, primary myoblasts isolated from the Ai9 mouse, which is a transgenic mouse strain containing stop codons in all 3 reading frames coupled to a triple poly(A) signal upstream of a tdTomato reporter, were electroporated with AsCpf1 RNP complexed with crRNAs with and without 5' extensions. The Ai9 mouse is a transgenic mouse strain, which contains a tdTomato reporter gene that has stop codons in all 3 reading frames coupled to a triple poly(A) signal. The AsCpf1 spacers were designed to introduce multiple breaks into the DNA that would result in the removal of the stop sequence through genomic deletion. Successful genetic editing is indicated by the expression of tdTomato (a red fluorescent protein, RFP), which can be visualized through fluorescence microscopy and quantified using flow cytometry. The extended crRNAs increased gene editing by 40-50% over the unextended crRNA. Myoblasts treated with unextended crRNA were 12% RFP positive; myoblasts treated with 2 nucleotide-extended crRNA were 15% RFP positive; myoblasts treated with 9 nucleotide-extended crRNA were 18% RFP positive, and myoblasts treated with 59 nucleotide-extended crRNA were 16% RFP positive (FIG. 10C). Additionally, the efficiency of gene editing was tested using the crRNA with ssDNA ssRNA (100 nt) with no sequence homology to target DNA primary myoblasts. Both ssDNA and ssRNA enhanced the gene editing efficiency (FIG. 10D).

Overall, the deletion of target sequence in primary myoblasts suggests that the enhanced gene editing of the extended crRNAs is broadly applicable across genetic targets and cell types. These results demonstrate that HD-RNA can be used as a therapeutic for genetic diseases.

Example 10

The following example demonstrates that enhancing gene editing effects of the 5' crRNA extensions are broadly applicable across genetic targets and cell types. These crRNAs were tested to see if they could enhance the ability of the Cpf1 RNP to edit an endogenous gene, using Serpina1, as a testbed.

Cpf1 with either crRNA or crRNA$+^{9}$, targeting the Serpina1 gene, were transfected into HepG2 cells were transfected using electroporation. Serpina1 was selected for further investigation because mutations in the Serpina1 gene cause alpha1-anti-trypsin deficiency, which makes it a target for therapeutic gene editing. Droplet digital PCR was conducted on genomic DNA from the HepG2 cells to quantify NHEJ efficiency.

Cpf1 RNP with crRNA$^{+9}$ had an enhanced NHEJ efficiency in comparison to wild type crRNA, as shown in FIG. 10E. These results further indicate that the gene editing effects of 5' crRNA extensions are broadly applicable across genetic targets.

All references, including publications, patent applications, and patents, cited herein are hereby incorporated by reference to the same extent as if each reference were individually and specifically indicated to be incorporated by reference and were set forth in its entirety herein.

The use of the terms “a” and “an” and “the” and “at least one” and similar referents in the context of describing the invention (especially in the context of the following claims) are to be construed to cover both the singular and the plural, unless otherwise indicated herein or clearly contradicted by context. The use of the term “at least one” followed by a list of one or more items (for example, “at least one of A and B”) is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A nucleic acid comprising a Cpf1 crRNA, wherein the Cpf1 crRNA comprises a stem-loop domain located 5' of a targeting sequence;

an extension sequence of at least 6 nucleotides 5' of the crRNA;

and, optionally, a processing sequence between the crRNA and the extension sequence, wherein the processing sequence is a sequence that is self-cleaved by Cpf1;

wherein the extension sequence does not comprise a processing sequence, an aptamer, or the sequence of the Cpf1 crRNA, and wherein the extension sequence comprises a nucleotide comprising a 2' deoxy modification.

2. The nucleic acid of claim 1, wherein the nucleic acid comprises a processing sequence, and the processing sequence comprises a fragment of a direct repeat sequence of a Cpf1 array, wherein the direct repeat sequence comprises a crRNA sequence portion and a processing portion positioned 5' of the crRNA sequence portion, and the fragment comprises at least 5 contiguous nucleotides of the processing portion of the direct repeat sequence.

3. The nucleic acid of claim 2, wherein the processing sequence comprises a fragment of at least 10 nucleotides of the processing portion of the direct repeat sequence.

4. The nucleic acid of claim 2, wherein the processing sequence comprises the entire processing portion of the direct repeat sequence.

5. The nucleic acid of claim 1, wherein the extension sequence comprises 10 to 100 nucleotides.

6. The nucleic acid of claim 1, wherein the nucleic acid contains only a single Cpf1 crRNA sequence.

7. The nucleic acid of claim 2, further comprising a second processing sequence 5' of the extension sequence, and a second extension sequence 5' of the second processing sequence.

8. The nucleic acid of claim 1, further comprising a donor nucleic acid hybridized or covalently linked thereto, optionally wherein: the donor nucleic acid is covalently linked 5' of the processing sequence, or 5' of the extension sequence; the donor nucleic acid is linked to the processing sequence or extension sequence by a linker group; or the donor nucleic acid is hybridized to the extension sequence and/or processing sequence.

9. The nucleic acid of claim 1, wherein the extension sequence comprises fewer than about 60 nucleotides.

10. The nucleic acid of claim 1, wherein the nucleic acid does not comprise a processing sequence.

11. The nucleic acid of claim 10, wherein the nucleic acid further comprises a donor nucleic acid covalently linked 5' of the extension sequence, optionally by a linker group, or hybridized to the extension sequence.

12. The nucleic acid of claim 1, wherein the extension sequence comprises a self-hybridizing sequence, optionally, a semi-stable hairpin structure, a stable hairpin structure, a pseudoknot structure, a G-quadraplex structure, a bulge loop structure, an internal loop structure, a branch loop structure, or a combination thereof.

13. The nucleic acid of claim 1, wherein the extension sequence or portion thereof is resistant to nuclease degradation.

14. The nucleic acid of claim 1, wherein the extension sequence comprises one or more modified internucleotide bonds.

15. The nucleic acid of claim 14, wherein a region of 4 or more contiguous nucleotides of the extension sequence, or the entire extension sequence, has modified internucleotide bonds.

16. The nucleic acid of claim 14, wherein the modified internucleotide bonds comprise phosphorothioate, phosphorodithioate, methylphosphonate, phosphoramidate, 2'-O-methyl, 2'-O-methoxyethyl, 2'-fluoro, bridged nucleic acid (BNA), or phosphotriester modified bonds, or a combination thereof, and/or wherein the extension sequence comprises one or more xeno nucleic acids (XNA).

17. The nucleic acid of claim 1, wherein the nucleic acid further comprises a biotin and/or avidin or streptavidin molecule attached to the 5' terminus of the extension sequence.

18. A composition comprising the nucleic acid of claim 1 and a carrier, and optionally further comprising a Cpf1 protein or nucleic acid encoding the Cpf1 protein.

19. The composition of claim 18, wherein the composition is substantially free of a divalent metal ion that promotes Cpf1 cleavage.

20. The composition of claim 18, wherein the composition comprises a cationic lipid.

21. The composition of claim 18, wherein the nucleic acid is in a liposome or partially or totally encapsulated by a polymer nanoparticle, or attached to a metal or polymer nanoparticle.

22. A method of genetically modifying a eukaryotic target cell, comprising contacting the eukaryotic target cell with the nucleic acid of claim 1 to genetically modify a target nucleic acid.

23. The method of claim 22, wherein the target cell is a mammalian cell, optionally a human cell.

24. The nucleic acid of claim 1, wherein the extension sequence comprises no more than 100 nucleotides.

25. A composition comprising (a) a nucleic acid comprising a Cpf1 crRNA, wherein the Cpf1 crRNA comprises a stem-loop domain located 5' of a targeting sequence;

an extension sequence of at least 4 nucleotides and no more than 100 nucleotides positioned 5' of the crRNA;

and, optionally, a processing sequence between the crRNA and the extension sequence, wherein the processing sequence is a sequence that is self-cleaved by Cpf1;

wherein the extension sequence does not comprise a processing sequence, an aptamer, or the sequence of the Cpf1 crRNA, and wherein the extension sequence comprises a nucleotide comprising a 2' deoxy modification; and (b) a liposome, polymer nanoparticle, or metal nanoparticle; wherein the nucleic acid is in the liposome, or partially or totally encapsulated by the polymer nanoparticle, or attached to the metal nanoparticle or polymer nanoparticle.

26. The composition of claim 25, wherein the composition comprises a Cpf1 protein, and the nucleic acid and Cpf1 protein is in the liposome or partially or totally encapsulated by the polymer nanoparticle, or attached to the metal or polymer nanoparticle.

27. The modified guide RNA of claim 1, wherein the extension sequence comprises 9 to 100 nucleotides.

28. The modified guide RNA of claim 27, wherein the extension sequence comprises 9 to 60 nucleotides.

29. A composition comprising (a) a nucleic acid comprising a Cpf1 crRNA, wherein the Cpf1 crRNA comprises a stem-loop domain located 5' of a targeting sequence;

an extension sequence of at least 4 nucleotides and no more than 100 nucleotides positioned 5' of the crRNA;

and, optionally, a processing sequence between the crRNA and the extension sequence, wherein the processing sequence is a sequence that is self-cleaved by Cpf1;

wherein the extension sequence does not comprise a processing sequence, an aptamer, or the sequence of the Cpf1 crRNA; and (b) a Cpf1 protein;

the nucleic acid and Cpf1 protein are in a liposome or partially or totally encapsulated by a polymer nanoparticle, or attached to a metal or polymer nanoparticle.

* * * * *